United States Patent [19]

Ollinger

[11] Patent Number: 4,468,388

[45] Date of Patent: Aug. 28, 1984

[54] PESTICIDAL N-(THIO)ACYL PHOSPHORODIAMIDO(DI)THIOATES

[75] Inventor: Janet Ollinger, Chalfont, Pa.

[73] Assignee: Rohm and Haas Company, Philadelphia, Pa.

[21] Appl. No.: 380,577

[22] Filed: May 21, 1982

[51] Int. Cl.$^3$ .......................... A01N 57/26; C07F 9/24
[52] U.S. Cl. .................................... 424/211; 260/938;
  260/940; 260/941; 260/946; 260/947; 260/948;
  260/949; 260/950; 260/951; 424/203; 424/210;
  424/215; 424/216; 424/217; 549/216
[58] Field of Search .................... 260/943, 455 P, 938,
  260/940, 941, 946, 947, 948, 949, 950, 951;
  424/212, 215, 210, 211, 216, 217; 549/216

[56] References Cited

U.S. PATENT DOCUMENTS

| | | | |
|---|---|---|---|
| 3,657,426 | 4/1972 | Schroeder | 424/200 |
| 3,716,600 | 2/1973 | Magee | 260/959 |
| 3,810,959 | 5/1974 | Gaughan | 260/941 |
| 3,887,657 | 6/1975 | Battershell et al. | 260/938 |
| 3,898,260 | 8/1975 | Meyer et al. | 260/455 P |
| 3,917,845 | 11/1975 | Brown | 424/215 |
| 3,957,924 | 5/1976 | Meyer et al. | 260/938 |
| 4,056,581 | 11/1977 | Bayer et al. | 260/972 |
| 4,161,524 | 7/1979 | Kishino et al. | 424/215 |
| 4,263,288 | 4/1981 | Ollinger | 424/210 |
| 4,279,897 | 7/1981 | Fahmy et al. | 424/211 |
| 4,315,870 | 2/1982 | Ollinger | 260/947 |

FOREIGN PATENT DOCUMENTS

| | | |
|---|---|---|
| 113551 | 8/1974 | German Democratic Rep. . |
| 2128325 | 4/1976 | Japan . |
| 464592 | 4/1973 | U.S.S.R. . |

*Primary Examiner*—Anton H. Sutto

[57] ABSTRACT

There are disclosed N-acyl and N-thioacyl phosphorodiamido(di)thioates having pesticidal activity when applied to pests or to loci to be freed from the pests by foliar or systemic application techniques.

24 Claims, No Drawings

PESTICIDAL N-(THIO)ACYL PHOSPHORODIAMIDO(DI)THIOATES

BACKGROUND OF THE INVENTION

1. Field of the Invention

This invention relates to novel N-acyl and N-thioacyl phosphorodiamido(di)thioates, and compositions thereof, which are useful as pesticides, more specifically, as acaricides, insecticides, and nematocides, when applied to pests or to loci to be freed from the pests by foliar or systemic application techniques, and to a method of controlling pests in agricultural plants.

2. Description of the Prior Art

Ollinger, U.S. Pat. No. 4,315,870, discloses acaricidal, insecticidal and nematocidal phosphorodiamidothioates represented by the formula

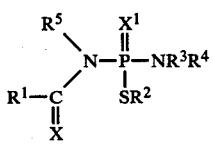

wherein $R^1$, $R^2$, $R^3$, $R^4$ and $R^5$ are selected from unsubstituted and substituted alkyl, alkenyl, alkynyl, phenyl and phenylalkyl groups and X and $X^1$ are selected from oxygen and sulfur atoms.

U.S. Pat. No. 4,279,897 discloses insecticidal compounds having the formula

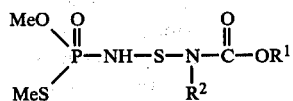

wherein $R^1$ is $C_1$-$C_{12}$ alkyl and $R^2$ is $C_2$-$C_8$ alkyl.

Russian Patent No. SU-464,592 discloses compounds having the formula

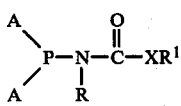

wherein R and $R^1$ are lower alkyl, X is O or S, and A is alkoxy, aryloxy, or amidomercapto.

Belgian Patent No. 804,757 discloses insecticidal compounds having the formula

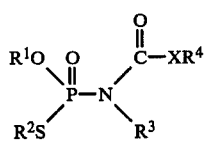

wherein $R^1$ is $C_1$-$C_4$ alkyl, $R^2$ and $C_1$-$C_7$ alkyl, $C_3$-$C_5$ alkenyl, $C_3$-$C_5$ alkynyl or optionally substituted benzyl, $R^3$ is $C_1$-$C_6$ alkyl, allyl or $C_3$-$C_6$ cycloalkyl, and $R^4$ is alkenyl, alkynyl, or optionally substituted benzyl, phenethyl, phenyl or naphthyl.

U.S. Pat. No. 3,810,959 discloses insecticidal compounds having the formula

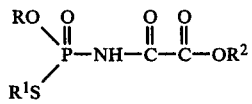

wherein R, $R^1$ and $R^2$ are $C_1$-$C_4$ alkyl.

German Patent No. DL 113,551 discloses biocidal compounds having the formula

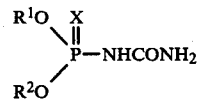

wherein X is O or S and $R^1$ and $R^2$ are aryl.

German Patent No. DT 2,447,095 discloses pesticidal compounds having the formula

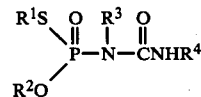

wherein $R^1$ is $C_3$-$C_5$ alkyl, $R^2$ is $CH_3$ or $C_2H_5$, $R^3$ is $C_1$-$C_4$ alkyl or $C_3$-$C_4$ alkenyl and $R^4$ is phenyl.

U.S. Pat. No. 3,887,657 discloses compounds having the formula

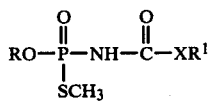

wherein R is alkyl, $R^1$ is aryl and X is O.

U.S. Pat. No. 3,917,845 discloses insecticidal compounds having the formula

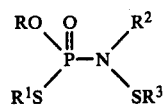

wherein R and $R^1$ are $C_1$-$C_3$ alkyl, alkenyl, or alkynyl, $R^2$ is H, $C_1$-$C_3$ alkyl or $SR^3$, and $R^3$ is $C_1$-$C_4$ alkyl optionally substituted by 1-4 F, Cl, or Br atoms or $C_6$-$C_{12}$ aryl.

DESCRIPTION OF THE INVENTION

It is an object of the invention to provide compounds, and compositions thereof, which possess pesticidal, more specifically, acaricidal, insecticidal, and nematicidal, activity and which have improved, that is to say, low phytotoxicity to agricultural plants and low mammalian toxicity relative to prior art compounds.

It is another object of the invention to provide a method of controlling pests, namely, acarides, insects, and nematodes.

These and other objects as will become apparent are achieved by the present invention which comprises compounds having the formula

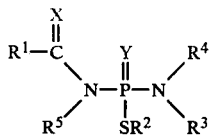

wherein
R[1] is hydrogen;
  unsubstituted or substituted $C_1$–$C_6$ alkyl wherein the substituent can be one cyano, nitro, alkoxy, alkylthio, alkylsulfinyl, alkysulfonyl, alkylcarbonyl, alkoxycarbonyl, alkylcarbonyloxy, phenoxy or phenylthio group or from one to three of the same or different bromo, chloro or fluoro groups;
  unsubstituted or substituted phenyl or naphthyl wherein the substituent can be from one to three of the same or different alkyl, haloalkyl, halo, alkoxy, alkylthio, cyano, nitro, or mono- or di-alkylamino, phenoxy, alkylsulfinyl, alkylsulfonyl, trifluoromethyl, alkoxycarbonyl, alkylcarbonyl, alkylcarbonyloxy, phenythio, phenysulfinyl, phenylsulfonyl, benzyl, phenylcarbonyl, phenylcarbonyloxy, phenylaminocarbonyl, alkenyloxycarbonyl, and alkenylcarbonyloxy wherein the alkyl moiety is straight or branched chain and contains from one to six carbon atoms $C_3$–$C_6$ alkenyl; and
  $C_3$–$C_8$ cycloalkyl;
$R^2$ is $C_2$–$C_6$ alkyl;
$R^3$ and $R^5$ are, independently, hydrogen, methyl or ethyl;
X and Y are, independently, O or S; and
$R^4$ is
(a) $SR^6$ wherein $R^6$ is unsubstituted or substituted $C_1$–$C_6$ alkyl wherein the substituent can be from one to three of the same or different chloro, bromo or fluoro groups; alkoxycarbonyl; unsubstituted or substituted phenyl or naphthyl wherein the substituent can be from one to three of the same or different alkyl, alkoxy, halo, cyano, nitro, alkylthio, alkylsulfinyl, alkylsulfonyl, phenoxy, haloalkyl, trifluoromethyl, mono- or di- alkylamino, alkylcarbonylamino, alkoxycarbonyl, alkylcarbonyl, alkylcarbonyloxy, phenylthio, phenylsulfinyl, phenylsulfonyl, benzyl, phenylcarbonyl, phenylcarbonyloxy, phenoxycarbonyl, phenylaminocarbonyl, alkenyloxycarbonyl, or alkenylcarbonyloxy, wherein the alkyl moiety is straight or branched chain and contains from one to six carbon atoms, unsubstituted or substituted amino wherein the substituent can be one or two of the same or different $C_1$–$C_6$ alkyl, unsubstituted or substituted phenyl ($C_1$–$C_5$) alkyl wherein the substituent is on the phenyl ring and wherein the substituent can be from one to three of the same or different alkyl, haloalkyl, halo, alkoxy, alkylthio, cyano, nitro, or mono- and di- alkylamino groups, wherein the alkyl moiety is straight or branched chain and contains from one to six carbon atoms;
(b) $SO_2R^6$ wherein $R^6$ is as defined above;
(c) $SN(R^7)C(=A)Z$ wherein $R^7$ is unsubstitited or substituted $C_1$–$C_6$ alkyl wherein the substituent can be from one to three of the same or different chloro, bromo or fluoro groups or one cyano, nitro, alkoxy, alkylthio, alkylsulfinyl, alkylsulfonyl, alkylcarbonyl, alkoxycarbonyl, alkylcarbonyloxy, mono- or di- alkylaminocarbonyl, alkylcarbonylamino, phenylthio, phenylsulfinyl, phenylsulfonyl, phenoxy, phenylcarbonyl, phenylcarbonyloxy, phenoxycarbonyl, phenylaminocarbonyl, alkenyloxycarbonyl, or alkenylcarbonyloxy groups, wherein the alkyl moiety is straight or branched chain and contains from one to six carbon atoms; unsubstituted or substituted phenyl or naphthyl, or unsubstituted or substituted phenyl($C_1$–$C_5$)alkyl, wherein the substituent on the phenyl or naphthyl ring can be from one to three of the same or different cyano, nitro, halo, alkyl, alkoxy, alkylthio, alkylsulfinyl, alkylsulfonyl, phenoxy, haloalkyl, trifluoromethyl, mono- or di- alkylaminocarbonyl, alkoxycarbonyl, alkylcarbonyl, alkylcarbonyloxy, phenylthio, phenylsulfinyl, phenylsulfonyl, benzyl, phenylcarbonyl, phenoxycarbonyl, phenylcarbonyloxy, phenylaminocarbonyl, alkenylcarbonyloxy, alkenylcarbonyloxy, aminocarbonyl, or alkylaminocarbonyl groups, wherein the alkyl moiety is straight or branched chain and contains from one to six carbon atoms; Z is unsubstituted $C_1$–$C_{10}$ alkoxy or $C_1$–$C_6$ alkoxy substituted with one alkylthio, alkoxy, or dialkylamino group, phenoxy, $C_1$–$C_6$ alkylthio, phenylthio, phenyl($C_1$–$C_5$)aklylthio, di-$C_1$–$C_6$ alkylamino, or $C_1$–$C_6$ alkyl; or benzofuranyl; and A is O or S;
(d) $CO_2R^8$ wherein $R^8$ is unsubstituted or substituted $C_1$–$C_6$ alkyl wherein the substituent can be from one to three bromo, chloro or fluoro groups, unsubstituted or substituted phenyl or naphthyl, or unsubstituted or substituted phenyl($C_1$–$C_3$)alkyl, wherein the substituent on the phenyl or naphthyl ring can be from one to three of the same or different cyano, nitro, halo, alkyl, alkoxy, alkylthio, alkylsulfinyl, alkylsulfonyl, phenoxy, haloalkyl, trifluoromethyl, mono- or di- alkylaminocarbonyl, alkoxycarbonyl, alkylcarbonyl, alkylcarbonyloxy, phenylthio, phenysulfinyl, phenylsulfonyl, benzyl, phenylcarbonyl, phenoxycarbonyl, phenylcarbonyloxy, phenylaminocarbonyl, alkenylcarbonyloxy, alkenylcarbonyloxy, aminocarbonyl, or alkylaminocarbonyl groups, wherein the alkyl moiety is straight or branched chain and contains from one to six carbon atoms; or $C_2$–$C_3$ alkenyl;
(e) $C(O)$-$C(O)$-$OR^9$ wherein $R^9$ is unsubstituted or substituted $C_1$–$C_{10}$ alkyl wherein the substituent can be from one to three of the same or different chloro, bromo or fluoro groups or one cyano, nitro, alkoxy, alkylthio, alkylsulfinyl, alkylsulfonyl, alkylcarbonyl, alkoxycarbonyl, alkylcarbonyloxy, mono- or di- alkylaminocarbonyl, alkylcarbonylamino, phenylthio, phenylsulfinyl, phenylsulfonyl, phenoxy, phenylcarbonyl, phenylcarbonyloxy, phenoxycarbonyl, phenylaminocarbonyl, alkenyloxycarbonyl, or alkenylcarbonyloxy groups, wherein the alkyl moiety is straight or branched chain and contains from one to six carbon atoms; unsubstituted or substituted phenyl or naphthyl or unsubstituted or substituted phenyl($C_1$–$C_3$)alkyl, wherein the substituents on the phenyl or naphthyl ring can be from one to three of the same or different cyano, nitro, halo, alkyl, alkoxy, alkylthio, alkylsulfinyl, alkylsulfonyl, phenoxy, haloalkyl, trifluoromethyl, mono- or di- alkylaminocarbonyl, alkoxycarbonyl, alkylcarbonyl, alkylcarbonyloxy, phenylthio, phenylsulfinyl, phenylsulfonyl, benzyl, phenylcarbonyl, phenoxycarbonyl, phenylcarbonyloxy, phenylaminocarbonyl, alkenylcarbonyloxy, alkenylcarbonyloxy, aminocarbonyl, or alkylaminocarbonyl groups, wherein the alkyl moiety is straight or branched chain and contains from one to six carbon atoms;

(f) $C(O)$-$NH(B)R^{10}$ wherein B is CO or $SO_2$; and $R^{10}$ is unsubstituted or substituted $C_1$-$C_6$ alkyl wherein the substituent can be from one to three bromo, chloro or fluoro groups; unsubstituted or substituted phenyl wherein the substituent can be from one to three of the same or different cyano, nitro, halo, alkyl, alkoxy, alkylthio, alkylsulfinyl, alkylsulfonyl, phenoxy, haloalkyl, trifluoromethyl, mono- or di- alkylaminocarbonyl, alkoxycarbonyl, alkylcarbonyl, alkylcarbonyloxy, phenylthio, phenylsulfinyl, phenylsulfonyl, benzyl, phenylcarbonyl, phenoxycarbonyl, phenylcarbonyloxy, phenylaminocarbonyl, alkenylcarbonyloxy, alkenylcarbonyloxy, aminocarbonyl, or alkylaminocarbonyl groups, wherein the alkyl moiety is straight or branched chain and contains from one to six carbon atoms;

(g) $C(O)NR^{11}R^{12}$ wherein $R^{11}$ and $R^{12}$ are, independently, hydrogen or unsubstituted or substituted $C_1$-$C_6$ alkyl wherein the substituent can be from one to three of the same or different chloro, bromo or fluoro groups or one cyano, nitro, alkoxy, alkylthio, alkylsulfinyl, alkylsulfonyl, alkylcarbonyl, alkoxycarbonyl, alkylcarbonyloxy, mono- or di- alkylaminocarbonyl, alkylcarbonylamino, phenylthio, phenylsulfinyl, phenylsulfonyl, phenoxy, phenylcarbonyl, phenylcarbonyloxy, phenoxycarbonyl, phenylaminocarbonyl, alkenyloxycarbonyl, or alkenylcarbonyloxy groups, wherein the alkyl moiety is straight or branched chain and contains from one to six carbon atoms.

(h) $(CHR^{14})_mS(O)_nR^{13}$ or $(CHR^{14})_mOR^{13}$ wherein m is 1, 2 or 3; n is 0, 1, or 2; $R^{13}$ is unsubstituted or substituted $C_1$-$C_6$ alkyl wherein the substituent can be from one to three of the same or different chloro, bromo or fluoro groups or one cyano, nitro, alkoxy, alkylthio, alkylsulfinyl, alkylsulfonyl, alkylcarbonyl, alkoxycarbonyl, alkylcarbonyloxy, mono- or di- alkylaminocarbonyl, alkylcarbonylamino, phenylthio, phenylsulfinyl, phenylsulfonyl, phenoxy, phenylcarbonyl, phenylcarbonyloxy, phenoxycarbonyl, phenylaminocarbonyl, or alkenylcarbonyloxy groups, wherein the alkyl moiety is straight or branched chain and contains from one to six carbon atoms; unsubstituted or substituted phenyl($C_1$-$C_3$)alkyl, or unsubstituted or substituted phenyl or naphthyl, wherein the substituent on the phenyl or naphthyl ring can be from one to three of the same or different cyano, nitro, halo, alkyl, alkoxy, alkylthio, alkylsulfinyl, alkylsulfonyl, phenoxy, haloalkyl, trifluoromethyl, mono- or di- alkylaminocarbonyl, alkoxycarbonyl, alkylcarbonyl, alkylcarbonyloxy, phenylthio, phenysulfinyl, phenylsulfonyl, benzyl, phenylcarbonyl, phenoxycarbonyl, phenylcarbonyloxy, phenylaminocarbonyl, alkenylcarbonyloxy, alkenylcarbonyloxy, aminocarbonyl, or alkylaminocarbonyl groups, wherein the alkyl moiety is straight or branched chain and contains from one to six carbon atoms; and $R^{14}$ is hydrogen; unsubstituted or substituted alkyl; or unsubstituted or substituted phenyl; or (i) $C(X)R^1$ wherein X and $R^1$ are as defined above.

Preferred are those compounds of formula I wherein:

X and Y are both O;
$R^1$ is hydrogen; unsubstituted or substituted $C_1$-$C_6$ alkyl; or unsubstituted or substituted phenyl;
$R^2$ is $C_2$-$C_6$ alkyl;
$R^3$ and $R^5$, independently, are hydrogen or methyl;
$R^4$ is
 (a) $SR^6$ wherein $R^6$ is unsubstituted or substituted $C_1$-$C_6$ alkyl; alkoxycarbonyl; or unsubstituted or substituted phenyl;
 (b) $SO_2R^6$ wherein $R^6$ is unsubstituted or substituted $C_1$-$C_6$ alkyl; alkoxycarbonyl; or unsubstituted or substituted phenyl;
 (c) $SN(R^7)C(=A)Z$ wherein $R^7$ is unsubstituted or substituted $C_1$-$C_6$ alkyl; unsubstituted or substituted phenyl; Z is unsubstituted $C_1$-$C_{10}$ or $C_1$-$C_6$ alkoxy substituted with one alkylthio, alkoxy, phenoxy, dialkylamino; $C_1$-$C_6$ alkylthio; phenylthio; benzofuranyl; phenyl($C_1$-$C_5$)alkylthio; di-($C_1$-$C_6$)alkylamino; or $C_1$-$C_6$ alkyl; and A is O or S;
 (d) $CO_2R^8$ wherein $R^8$ is unsubstituted or substituted $C_1$-$C_6$ alkyl; unsubstituted or substituted phenyl, or unsubstituted or substituted phenyl($C_1$-$C_3$)alkyl; or $C_2$-$C_3$ alkenyl;
 (e) $C(O)$-$C(O)$-$OR^9$ wherein $R^9$ is unsubstituted or substituted alkyl, unsubstituted or substituted phenyl, or unsubstituted or substituted phenyl($C_1$-$C_3$)alkyl;
 (f) $C(O)$-$NH(B)R^{10}$ wherein B is CO or $SO_2$; and $R^{10}$ is unsubstituted or substituted $C_1$-$C_6$ alkyl wherein the substituent can be from one to three of the same or different bromo, chloro or fluoro groups; or unsubstituted or substituted phenyl wherein the substituent can be one to three of the same or different alkyl or halo groups;
 (g) $C(O)NR^{11}R^{12}$ wherein $R^{11}$ and $R^{12}$, are independently, hydrogen or unsubstituted $C_1$-$C_6$ alkyl;
 (h) $(CHR^{14})_mS(O)_nR^{13}$ or $(CHR^{14})_mOR^{13}$ wherein m is 1, 2 or 3; n is 0, 1 or 2; $R^{13}$ is unsubstituted or substituted $C_1$-$C_6$ alkyl; and $R^{14}$ is hydrogen or unsubstituted $C_1$-$C_6$ alkyl; or
 (i) $C(X)R^1$ wherein
  X is O; and
  $R^1$ is hydrogen; unsubstituted or substituted $C_1$-$C_6$ alkyl; or unsubstituted or substituted phenyl.

These compounds are preferred because they are illustrative of the scope of the compounds conceived as the invention, which compounds provide a useful combination of low mammalian toxicity, low phytotoxicity to agricultural plants, and pesticidal efficacy.

More preferred are those compounds of formula I wherein:

$R^1$ is hydrogen; unsubstituted or substituted $C_1$-$C_6$ alkyl wherein the substituent can be from one to three of the same or different bromo, chloro or fluoro groups; or phenyl;
$R^2$ is $C_3$-$C_5$ alkyl;
$R^3$ and $R^5$ are each methyl; and
$R^4$ is
 (a) $SR^6$ wherein $R^6$ is unsubstituted or substituted $C_1$-$C_6$ alkyl wherein the substituent can be from one to three of the same or different chloro, bromo, or fluoro groups; unsubstituted or substituted phenyl wherein the substituent can be from one to three of the same or different alkyl groups; or alkoxycarbonyl;

(b) $SO_2R^6$ wherein $R^6$ is unsubstituted $C_1-C_6$ alkyl or trifluoromethyl or unsubstituted phenyl;

(c) $SN(R^7)C(=A)Z$ wherein $R^7$ is unsubstituted or substituted $C_1-C_6$ alkyl; A is O; and Z is $C_1-C_{10}$ alkoxy or benzofuranyl;

(d) $CO_2R^8$ wherein $R^8$ is unsubstituted or substituted $C_1-C_6$ alkyl wherein the substituent can be from one to three of the same or different bromo, chloro, or fluoro groups; unsubstituted phenyl; unsubstituted phenyl ($C_1-C_3$) alkyl; and $C_2-C_3$ alkenyl;

(e) $C(O)-C(O)-OR^9$ wherein $R^9$ is unsubstituted or substituted $C_1-C_{10}$ alkyl;

(f) $C(O)-NH(B)R^{10}$ wherein B is $C(O)$ or $SO_2$; and $R^{10}$ is unsubstituted or substituted $C_1-C_6$ alkyl wherein the substituent can be from one to three of the same or different bromo, chloro or fluoro groups; unsubstituted or substituted phenyl wherein the substituent can be from one to three alkyl groups;

(g) $C(O)NR^{11}R^{12}$ wherein $R^{11}$ and $R^{12}$ are, independently, hydrogen or $C_1-C_3$ alkyl;

(h) $(CH_2)_mSR^{13}$ or $(CH_2)_mOR^{13}$ wherein m is 1 or 2; and $R^{13}$ is unsubstituted $C_1-C_6$ alkyl; or (i) $C(X)R^1$ wherein X and $R^1$ are as defined above.

These compounds are more preferred because they embrace the scope of the compounds shown to provide a usefully and advantageous combination of low mammalian toxicity, low phytotoxicity to agricultural plants and pesticidal efficacy. Also, these compounds can be conveniently produced from readily accessible materials.

Most preferred are those compounds of formula I wherein:

X and Y are O;
$R^1$ is hydrogen, methyl, phenyl or trifluoromethyl;
$R^2$ is 1-methylpropyl;
$R_3$ and $R_5$ are each methyl; and
$R^4$ is (a) $SR^6$ wherein $R^6$ is phenyl, 4-methylphenyl, methyl or trichloromethyl, or methoxycarbonyl;

(b) $SO_2R^6$ wherein $R^6$ is methyl, butyl, trifluoromethyl;

(c) $SN(R^7)C(=A)Z$ wherein $R^7$ is methyl and $C(=A)Z$ is $C(O)OPr$, $C(O)OEt$, $C(O)OCH(CH_3)CH_3$ or $C(O)OC_{10}H_{21}$;

(d) $CO_2R^8$ wherein $R^8$ is phenylmethyl, 2-trichloroethyl, or $-CH=CH_2$;

(e) $C(O)-C(O)-OR^9$ wherein $R^9$ is methyl 1-methylethyl, ethyl, or 2-methoxyethyl (f) $C(O)-NH(B)R^{10}$ wherein B is $SO_2$ or $C(O)$ and $R^{10}$ is 4-methylphenyl, phenyl, or trichloromethyl (g) $C(O)NR^{11}R^{12}$ wherein $R^{11}$ is hydrogen and $R^{12}$ is methyl;

(h) $CH_2SCH_3$; or (i) $C(X)R^1$ wherein X is O and $R^1$ is hydrogen or trifluoromethyl.

These compounds are most preferred because they have been shown to provide an especially useful and advantageous combination of low mammalian toxicity, low phytotoxicity to agricultural plants and pesticidal efficacy. Further, these compounds have been conveniently produced from readily accessible materials.

In another aspect, the invention comprises a pesticidal composition comprising a pesticidally effective amount of the compound of formula I and an agronomically acceptable carrier.

In yet another aspect, the invention comprises a method of controlling pests comprising applying to the pests or to the loci to be freed from infestation by the pests a pesticidally effective amount of the compound of formula I.

As used in the specification and claims, the terms "alkyl", "alkenyl" and "alkynyl" are meant to include branched as well as straight chain alkyl, alkenyl and alkynyl groups. Representative examples of such groups include methyl, ethyl, propyl, isopropyl, sec-butyl, isobutyl, tert-butyl, pentyl, neopentyl, hexyl, allyl, 2-butenyl, 3-methyl-1-pentenyl, 3-hexynyl, propynyl, 1-pentynyl, 4-methyl-1-pentynyl, hexynyl, and the like.

By "substituted phenyl or naphthyl", as used in the specification and claims, is meant a phenyl or naphthyl group substituted with one or more, but preferably with one to three, substituents selected from cyano, nitro, halo, alkyl, alkoxy, alkylthio, alkylsulfinyl, alkylsulfonyl, phenoxy, haloalkyl, trifluoromethyl, mono- or dialkylaminocarbonyl, alkoxycarabonyl alkylcarbonyl, alkylcarbonyloxy, phenylthio, phenylsulfinyl, phenylsulfonyl, benzyl, phenylcarbonyl, phenoxycarbonyl, phenylcarbonyloxy, phenylaminocarbonyl, alkenyloxycarbonyl, alkenylcarbonyloxy, aminocarbonyl and alkylcarbonylamino and the like, wherein each alkyl moiety is straight or branched chain and contains from 1 to 6 preferable from 1 to 4 more preferably 1 or 2 carbon atoms.

By "substituted alkyl", as used in the specification and claims, is meant a ($C_1-C_{12}$) alkyl group, preferably ($C_1-C_6$), more preferably ($C_1-C_4$), substituted with one to three halo groups, particularly selected from chloro, bromo, or fluoro; or one substituent selected from cyano, nitro, alkoxy, alkylthio, alkylsulfinyl, alkylsulfonyl, alkylcarbonyl, alkoxycarbonyl, alkylcarbonyloxy, mono- or dialkylaminocarbonyl, alkylcarbonylamino, and the like, wherein each alkyl moiety is straight or branched chain, and contains from 1 to 6, preferably from 1 to 4, more preferably 1 to 2, most preferably 1 carbon atom(s); alkenyloxycarbonyl and alkenylcarbonyloxy wherein the alkenyl moiety contains from 3 to 6 preferably from 3 to 4 carbon atoms; and phenoxy, phenylthio, phenylsulfinyl, phenylsulfonyl, phenylcarbonyl, phenyloxycarbonyl, phenylcarbonyloxy, phenylaminocarbonyl, and the like, wherein the phenyl is optionally substituted (but preferably unsubstituted) with substituents such as defined above for substituted phenyl; and aminocarbonyl.

By "alkenyl", as used in the specification and claims, is meant an alkenyl group, such as an allyl group, with one cis or trans double bond.

By "alkynyl", as used in the specification and claims, is meant an alkynyl group, such as a propargyl group, with one triple bond.

By "substituted phenyl($C_1-C_5$)alkyl" is meant a phenyl($C_1-C_5$)alkyl group, e.g., benzyl, phenethyl, 3-phenyl-1-methylpropyl, etc., the phenyl ring of which is substituted with one or more, preferably with one to three, substituents selected from the group of substituents defined for substituted phenyl above. Representative compounds of the invention are listed below:

N,N'-Dimethyl S-(1-methylpropyl) N'-methylthio N-(4-nitrophenyl)carbonyl phosphorodiamidothioate N-Methylthiocarbonyl N,N'-diethyl N'-hexylthio S-propyl phosphorodiamidothioate N-Hexylthiocarbonyl N,N'-dimethyl N'(4-nitrophenyl)thio S-propyl phosphorodiamidothioate N-[(2-Ethoxycarbonylpropyl)carbonyl] N,N'-dimethyl N'-(methoxycarbonyl)thio S-(1-methylpropyl) phosphorodiamidothioate N,N'-Diethyl N-(2-methoxyethylcarbonyl) S-propyl N'-trichloromethylthio phosphorodiamidothioate N-Hydrogenthiocarbonyl N,N'-dimethyl S-(1-methylpropyl) N'-phenylthio phosphorodiamidothioate N-Ethyl N'-methyl N-methylcarbonyl S-(1-methylpropyl) N'-(2-methylphenyl)thio phosphorodiamidothioate N'-(4-Chlorophenyl)thio N-hexylcarbonyl N,N'-dimethyl S-propyl phosphorodiamidothioate N-Hydrogencarbonyl N,N'-dimethyl S-ethyl N'-propylthio phosphorodiamidothioate N,N'-Diethyl N-ethylcarbonyl S-(2-methylpropyl) N'-trichloromethylthio phosphorodiamidothioate N-Ethylcarbonyl N,N'-dimethyl S-hexyl N'-hexylthio phosphorodiamidothioate N,N'-Diethyl N-hydrogenthiocarbonyl S-propyl N'-methylthio phosphorodiamidothioate N-Hydrogencarbonyl N,N'-dimethyl N'-ethylthio S-(1-methylpropyl) phosphorodiamidothioate S-Butyl N',N-diethyl N'-(4-methylphenyl)thio N-methylthiocarbonyl N'-propylthio phosphorodiamidothioate N-Methylcarbonyl N,N'-dimethyl N'-(4-methylphenyl)thio S-propyl phosphorodiamidothioate N-Chloromethylcarbonyl N,N'-diethyl N'-(2,4-dinitrophenyl)thio S-(1-methylpropyl) phosphorodiamidothioate N-Hydrogenthiocarbonyl N,N'-dimethyl S-hexyl N'-propylthio phosphorodiamidothioate N-Hydrogencarbonyl S-hexyl N,N'-dimethyl N'-methanesulfonyl phosphorodiamidothioate N,N'-Diethyl N-methylcarbonyl S-(2-methylpropyl) N'-phenylsulfonyl phosphorodiamidothioate N,N'-Dimethyl S-ethyl N-ethylcarbonyl N'-hexanesulfonyl phosphorodiamidothioate N'-(4-Chlorophenyl)sulfonyl N-hydrogencarbonyl N,N'-dimethyl S-propyl phosphorodiamidothioate N'-(4-methylphenyl)sulfonyl N,N'-dimethyl N-methylthiocarbonyl S-propyl phosphorodiamidothioate N,N'-Dimethyl N-hydrogenthiocarbonyl N'-propylsulfonyl S-propyl phosphorodiamidothioate N'-Butylsulfonyl N,N'-diethyl N-hydrogencarbonyl S-pentyl phosphorodiamidothioate N'-Hexanesulfonyl N,N'-dimethyl N-methylthiocarbonyl phosphorodiamidothioate S-Hexyl N-hydrogenthiocarbonyl N,N'-dimethyl N'-trifluoromethylsulfonyl phosphorodiamidothioate N-Butylcarbonyl N,N'-diethyl S-pentyl N'-propylsulfonyl phosphorodiamidodithioate S-Hexyl N-hexanecarbonyl N,N'-dimethyl N'-trifluoromethylsulfonyl phosphorodiamidothioate N,N'-Diethyl N-methanesulfonyl N'-methylthiocarbonyl S-propyl phosphorodiamidodithioate S-Butyl N-(3-hexenyl)carbonyl N'-pentylsulfonyl N,N'-dimethyl phosphorodiamidothioate N-Methoxymethylcarbonyl N'-methanesulfonyl N,N'-dimethyl S-pentyl phosphorodiamidothioate N-Cyclohexylcarbonyl N,N'-dimethyl S-pentyl N'-phenylsulfonyl phosphorodiamidothioate N,N'-Diethyl S-(1-methylpropyl) N-phenylcarbonyl N'-propylsulfonyl phosphorodiamidothioate N-Benzylcarbonyl N,N'-dimethyl N-methanesulfonyl S-(1-methylethyl) phosphorodiamidothioate S-Ethyl N,N'-dimethyl N-methoxymethylcarbonyl N'-phenylsulfonyl phosphorodiamdodithioate N'-[Methoxycarbonyl(methyl)amino]thio N,N'-dimethyl S-propyl N-trifluoromethylcarbonyl phosphorodiamidothioate N,N',S-Triethyl N-hydrogencarbonyl S-(2-methylethyl) N'-[phenoxycarbonyl (hexyl)amino]thio phosphorodiamidothioate S-Hexyl N'-[(2-methoxy)ethoxycarbonyl(phenyl)amino]thio N,N'-dimethyl N-(2-propenyl)carbonyl phosphorodiamidothioate N,N'-Dimethyl N'-[(2-dimethylamino)ethoxycarbonyl(benzyl)amino]thio S-(2-methylpropyl) N-phenylcarbonyl phosphorodiamidothioate N,N'-Dimethyl N'-[1-methylethoxycarbonyl(methyl)-amino]thio S-propyl N-trifluoromethylcarbonyl phosphordiamidodithioate N,N'-Dimethyl S-(2-methylpropyl) N'-[propoxythiocarbonyl(propyl)amino]thio N-phenylcarbonyl phosphorodiamidothioate N-Hydrogenthiocarbonyl N,N'-dimethyl S-pentyl N'-[phenoxycarbonyl(propyl)amino]thio phosphorodiamidodithioate N-(Methoxycarbonyl)methylcarbonyl N,N'-dimethyl S-(2-methylbutyl) N'-[phenoxycarbonyl(benzyl)amino]thio phosphordiamidodithioate N-(3-Hexenyl)thiocarbonyl N'-[methoxythiocarbonyl(methyl)amino N,N'-dimethyl S-propyl phosphorodiamidodithioate N'-[Benzyloxycarbonyl(benzyl)amino]thio S-butyl N,N'-dimethyl N-methylcarbonyl phosphorodiamidodithioate N'-[Decyloxycarbonyl(propyl)amino]thio S-hexyl N,N'-dimethyl N-methylthiocarbonyl phosphorodiamidodithioate N,N'-Diethyl N-ethylcarbonyl N'-[(methylthio)carbonyl(methyl)amino]thio S-propyl phosphorodiamidothioate N'-[(Hexylthio)carbonyl(propyl)amino]thio N,N'-dimethyl N-methylcarbonyl S-[1-methylpropyl) phosphorodiamidothioate S-Butyl N'-[(4-chlorophenylthio)carbonyl(benzyl)-amino]thio N,N'-diethyl N-trifluoromethylcarbonyl phosphorodiamidothioate N-Chloromethylcarbonyl N,N'-diethyl N'-[(phenylthio)thiocarbonyl(methyl)amino]thio phosphorodiamidothioate N-(2-Ethoxycarbonylpropyl)carbonyl N,N'-diethyl N'-[(hexylthio)thiocarbonyl(hexyl)amino]thio S-(1-methylpropyl) phosphorodiamidothioate N'-[(Benzylthio)carbonyl(phenyl)amino]thio N,N'-dimethyl S-(1-methylpropyl N-(4-nitrophenyl)carbonyl phosphorodiamidothioate N'-[(Benzylthio)carbonyl(methyl)amino]thio N,N'-hydrogenthiocarbonyl S-propyl phosphorodiamidothioate N'-[(Benzylthio)carbonyl(hexyl)amino]thio N-(ethoxycarbonyl)methylcarbonyl N,N'-dimethyl S-(1-methylbutyl phosphorodiamidodithioate N'-[(Ethylthio)thiocarbonyl(ethyl)amino]thio N,N'-dimethyl N-methylthiocarbonyl S-propyl phosphorodiamidodithioate N-Cyclohexylcarbonyl N'-ethyl N'-[(ethylthio)-carbonyl(cyclohexyl)amino]thio N-methyl S-(2-methylpentyl) phosphorodiamidothioate N-Cyclopropylcarbonyl N,N'-dimethyl N'-[(dimethylaminocarbonyl(ethyl)amino]thio S-(1-methylethyl) phosphorodiamidothioate N-Hydrogencarbonyl N,N'-dimethyl N'-[dimethylaminocarbonyl(ethyl)amino]thio S-propyl phosphorodiamidodithioate N'-[Dihexylaminocarbonyl(hexyl)amino]thio N,N'-dimethyl N-methylthiocarbonyl S-(1-methylethyl) phosphorodiamidothioate S-Butyl N,N'-diethyl N'-[dimethylaminothiocarbonyl-(methyl)amino]thio S-(2-methylpropyl) N-trifluoromethylcarbonyl phosphorodiamidothioate S-Ethyl N'-[diethylaminocarbonyl(propyl)amino]thio N,N'-dimethyl N-trifluoromethylthiocarbonyl phosphorodiamidothioate S-Hexyl N'-[dimethylaminocarbonyl(benzyl)amino]thio N,N'-dimethyl N-methylthiocarbonyl phosphorodiamidodithioate N-Hydrogenthiocarbonyl N'-dimethylaminothiocarbonyl-(benzyl)amino]thio N,N'-dimethyl S-(2-methylpropyl) phosphorodiamidodithioate N-Cyclohexylcarbonyl N,N'-dimethyl N'-dimethylaminocarbonyl(4-chlorophenyl)amino]thio S-(1-methylethyl) phosphorodiamidothioate N'-[Diethylaminothiocarbonyl(hexyl)amino]thio N,N'-dimethyl S-(1-methylbutyl) N-(2-propenyl)-carbonyl phosphorodiamidothioate N'-[Diethylaminothiocarbonyl(methyl)amino]thio N,N'-dimethyl S-(1-methylethyl) N-phenylcarbonyl phosphorodiamidodithioate N,N'-Dimethyl N-methylcarbonyl (methyl)amino]thio S-propyl phosphorodiamidothioate N'-Hexylcarbonyl(methyl)amino]thio N,N'-dimethyl N-(2-propenyl)carbonyl S-propyl phosphorodiamidodithioate N-Hydrogenthiocarbonyl N,N'-dimethyl N'-[propylcarbonyl(hexyl)amino]thio S-propyl phosphorodiamidothioate N-Hydrogencarbonyl N,N'-dimethyl N'-[methylthiocarbonyl(benzyl)amino]thio S-pentyl phosphorodiamidothioate N-Hydrogencarbonyl N,N'-dimethyl S-(1-methylpropyl) N'-[methylthiocarbonyl(phenyl)amino]thio phosphorodiamidodithioate S-(1-Ethylpropyl) N,N'-dimethyl N-methylthiocarbonyl-N'-[pentylcarbonyl(ethyl)amino]thio phosphorodiamidodithioate N'-Methoxycarbonyl N,N'-dimethyl S-(1-methylpropyl) N-(4-nitrophenyl)carbonyl phosphorodiamidothioate N-Hexylcarbonyl N'-hexyloxycarbonyl N,N'-dimethyl S-propyl phosphorodiamidothioate N'-Ethoxycarbonyl S-ethyl N-hydrogenthiocarbonyl N,N'-dimethyl phosphorodiamidothioate S-Butyl N,N'-diethyl N'-phenoxycarbonyl N-trifluoromethanecarbonyl phosphorodiamidothioate N'-Benzyloxycarbonyl N,N'-dimethyl N-methylthiocarbonyl S-propyl phosphorodiamidothioate N,N'-Dimethyl N-methoxymethylcarbonyl S-(2-methylpentyl) N'-(2-trichloroethoxycarbonyl) phosphorodiamidothioate N-Chloromethylthiocarbonyl N'-(4-chlorophenoxycarbonyl) N,N'-dimethyl S-propyl phosphorodiamidothioate N'-Ethenyloxycarbonyl N,N'-diethyl N-hydrogenthiocarbonyl S-propyl phosphorodiamidothioate N-Methylthiocarbonyl N,N'-diethyl N-hydrogenthiocarbonyl S-propyl phosphorodiamidothioate N-Hydrogencarbonyl N,N'-dimethyl N'-(1-propenyloxycarbonyl) S-propyl phosphorodiamidodithioate N-Hexylthiocarbonyl N,N'-dimethyl N'(propyloxycarbonyl) S-propyl phosphorodiamidothioate N,N'-Diethyl N-ethylcarbonyl N'-ethoxycarbonyl S-(2-methylpropyl) phosphorodiamidodithioate N-Cyclopropylcarbonyl N'-ethoxycarbonyl S-ethyl N,N'-dimethyl phosphorodiamidothioate N-Cyclohexylcarbonyl N,N'-dimethyl S-pentyl N'-(pentyloxycarbonyl) phosphorodiamidothioate S-Butyl N,N'-diethyl N'-methoxycarbonyl N-(methoxycarbonylethyl)carbonyl phosphorodiamidodithioate N-Benzylcarbonyl N,N'-diethyl N'-(ethoxycarbonyl) S-hexyl phosphorodiamidothioate N-(Ethoxycarbonyl)methylcarbonyl N,N'-diethyl N-(2-methylethoxycarbonyl) S-(1-methylbutyl) phosphorodiamidodithioate N'-(Butyloxycarbonyl) N-chloromethylcarbonyl N,N'-dimethyl S-propyl phosphorodiamidothioate N'-(Decyloxycarbonyl)carbonyl N-hydrogencarbonyl N,N'-dimethyl S-propyl phosphorodiamidothioate N'-(Decyloxycarbonyl)carbonyl N-hexylcarbonyl N-hexylcarbonyl N,N'-dimethyl S-pentyl phosphorodiamidothioate N,N',S-Triethyl N'-(methoxycarbonyl)carbonyl N-trifluoromethanecarbonyl phosphorodiamidothioate N'-(Benzyloxycarbonyl)carbonyl S-butyl N,N'-dimethyl N-methylcarbonyl phosphorodiamidothioate N'-(4-Bromobenzyloxycarbonyl)carbonyl N,N'-dimethyl S-(1-methylpropyl) N-phenylcarbonyl phosphorodiamidothioate N-(Methoxymethylcarbonyl) N,N'-dimethyl S-(2-methylpropyl) N'-(phenoxycarbonyl)carbonyl phosphorodiamidothioate N-(Hydrogenthiocarbonyl) N,N'-dimethyl N'-(1-methylethoxycarbonyl)carbonyl S-(2-methylpropyl) phosphorodiamidothioate N-Cyclohexylcarbonyl N'-(ethoxycarbonyl)carbonyl N,N'-dimethyl S-pentyl phosphorodiamidodithioate S-Butyl N,N'-diethyl N'-(ethoxycarbonyl)carbonyl N-(2-propenyl) phosphorodiamidodithioate S-Ethyl N,N'-dimethyl N'-(3-hexenyl)carbonyl N-methylthiocarbonyl phosphorodiamidodithioate N,N'-Dimethyl N'-(methoxycarbonyl)carbonyl S-pentyl N-trichloromethylthiocarbonyl phosphorodiamidodithioate N'-(Benzyloxycarbonyl)carbonyl S-butyl N-hydrogenthiocarbonyl N,N'-dimethyl phosphorodiamidothioate S-Ethyl N,N'-dimethyl N-(2-propenyl)carbonyl N'-(propyloxycarbonyl)carbonyl phosphorodiamidodithioate N'-(Benzyloxycarbonyl)carbonyl N-(3-hexynyl)carbonyl N,N'-dimethyl S-propyl phosphorodiamidodithioate N'-(4-Chlorophenoxycarbonyl)carbonyl N-ethylthiocarbonyl N,N'-dimethyl S-(1-methylethyl) phosphorodiamidodithioate Hydrogenthiocarbonyl N'-(4-methoxyphenoxycarbonyl)carbonyl N,N'-dimethyl S-(1-methylpentyl) phosphorodiamidothioate S-Butyl N-cyclohexylthiocarbonyl N'-(ethoxycarbonyl)carbonyl N,N'-diethyl phosphorodiamidodithioate N-Chloromethylcarbonyl N,N'-diethyl S-(1-methylethyl) N'-(phenoxycarbonyl)carbonyl phosphorodiamidodithioate N,N',S-Triethyl N'-(methoxycarbonyl)carbonyl N-methylthiocarbonyl phosphorodiamidodithioate N,N'-Dimethyl N'-(methylsulfonylaminocarbonyl) S-pentyl N-trifluoromethylcarbonyl phosphorodiamidothioate N,N'-Dimethyl N'-(methylcarbonylaminocarbonyl) S-pentyl N-trifluoromethylcarbonyl phosphorodiamidothioate N'-(Hexylsulfonylaminocarbonyl) N,N'-dimethyl S-(1-methylpropyl) N-trichloromethylcarbonyl phosphorodiamidothioate N'-(Hexylcarbonylaminocarbonyl) N,N'-dimethyl N-methylcarbonyl S-(1-methylethyl) phosphorodiamidothioate N,N',S-Triethyl N-hydrogencarbonyl N'-(phenysulfonylaminocarbonyl) S-(2-methylpropyl) phosphorodiamidothioate N,N'-Dimethyl N-hydrogenthiocarbonyl N'-(4-methylphenylsulfonylaminocarbonyl) S-(1-methylpropyl) phosphorodiamidothioate N,N'-Dimethyl N-hydrogenthiocarbonyl N'-(4-methylphenylcarbonylaminocarbonyl) S-(2-methylpropyl) phosphorodiamidothioate N-Cyclopropylcarbonyl N,N'-dimethyl S-propyl N'-(trichloromethanesulfonylaminocarbonyl) phosphorodiamidothioate N-Cyclohexylcarbonyl N,N'-dimethyl S-propyl N'-(trichloromethanecarbonylaminocarbonyl) phosphorodiamidothioate S-Butyl N-chloromethylcarbonyl N,N'-dimethyl N'-[(4-methoxyphenyl)sulfonylaminocarbonyl] phosphorodiamidothioate S-Butyl N-chloromethylcarbonyl N,N'-dimethyl N'-[(4-methoxyphenyl)carbonylaminocarbonyl] phosphorodiamidothioate S-Hexyl N-methoxymethylcarbonyl N,N'-dimethyl N'-(2-methylphenylsulfonylaminocarbonyl) phosphorodiamidothioate N-Hexylcarbonyl N,N'-dimethyl N'-(2-methylphenylcarbonylaminocarbonyl) phosphorodiamidothioate N-Hexylcarbonyl N,N'-dimethyl N'-(4-methoxyphenylsulfonylaminocarbonyl) phosphorodiamidothioate N-Hydrogenthiocarbonyl N'-(4-methoxyphenylsulfonylaminocarbonyl) phosphorodiamidothioate N-Hydrogenthiocarbonyl N'-(2-methoxyphenylcarbonylaminocarbonyl) N,N'-dimethyl S-(2-methylethyl) phosphorodiamidothioate N-Hydrogencarbonyl N,N'-(dimethylamino)carbonyl S-propyl phosphorodiamidothioate N,N'-Dimethyl N'-(methylamino)carbonyl N-methylcarbonyl S-(1-methylethyl) phosphorodiamidothioate N'-(Hexylamino)carbonyl N,N'-dimethyl S-pentyl N-phenylcarbonyl phosphorodiamidothioate N-Benzylcarbonyl S-butyl N'-(dihexylamino)carbonyl N,N'-dimethyl phosphorodiamidothioate N-Cyclopropylthiocarbonyl N,N',S-triethyl N'-(diethylamino)carbonyl phosphorodiamidothioate N,N'-Diethyl S-butyl N-methoxymethylcarbonyl N'-(propylamino)carbonyl phosphorodiamidodithioate N-(4-Chlorophenylcarbonyl) N,N'-dimethyl S-(1-methylpropyl) N'-[methyl(propyl)amino]carbonyl phosphorodiamidodithioate N'-(Diethylamino)carbonyl N-(4-methoxyphenyl)carbonyl N,N'-dimethyl S-(2-methylpropyl) phosphorodiamidodithioate S-(1-Ethylpropyl) N-ethylthiocarbonyl) N,N'-dimethyl N-(methylamino)carbonyl phosphorodiamidodithioate N-Hydrogencarbonyl N,N'-dimethyl S-(1-methylethyl) N'-(methylthiomethyl) phosphorodiamidothioate S-Butyl N,N'-diethyl N-methylcarbonyl N'-(methylthioethyl) phosphorodiamidothioate S-Ethyl N-hexylcarbonyl N,N'-dimethyl N'-(methylsulfinylmethyl) phosphorodiamidothioate S-Butyl N-cyclopropylcarbonyl N'-(hexylthiomethyl) N,N'-dimethyl phosphorodiamidothioate N-Cyclohexylcarbonyl N,N'-diethyl N'-(hexylthiomethyl) S-(2-methylpropyl) phosphorodiamidodithioate N-Chloromethylcarbonyl N'-(hexylsulfinylmethyl) N,N'-dimethyl S-(1-methylpropyl) phosphorodiamidothioate S-Hexyl N'-(hexylsulfonylmethyl) N-methylthiocarbonyl N,N'-dimethyl phosphorodiamidothioate S-Butyl N-methoxymethylcarbonyl N,N'-dimethyl S-(2-methylpropyl) N'-(methylsulfonylmethyl) phosphorodiamidothioate S-Butyl N-hydrogenthiocarbonyl N,N'-dimethyl N'-(phenylthiomethyl) phosphorodiamidothioate N,N'-Diethyl S-hexyl N'-(4-methoxyphenylthiomethyl) N-methylcarbonyl phosphorodiamidothioate N'-(4-Chlorophenylthiomethyl) S-ethyl N-methoxymethylcarbonyl N,N'-dimethyl phosphorodiamidothioate N'-(4-Chlorophenylsulfinylethyl) S-hexyl N-hydrogenthiocarbonyl N,N'-dimethyl phosphorodiamidothioate N,N'-Diethyl S-pentyl N-phenylcarbonyl N'-(phenylsulfinylmethyl) phosphorodiamidothioate N'-(Benzylthiomethyl) N,N',S-triethyl N-(2-propenyl) phosphorodiamidothioate N'-(2-Methoxyphenylsulfonylmethyl) N,N'-dimethyl N-methylcarbonyl S-pentyl phosphorodiamidodithioate N'-(Benzylthiomethyl) S-butyl N-(3-hexynylcarbonyl) N,N'-dimethyl N-methylthiocarbonyl phosphorodiamidodithioate N'-(Benzylsulfinylethyl) N-(3-hexenylcarbonyl) S-hexyl N,N'-dimethyl phosphorodiamidothioate N'-(Benzylsulfonylmethyl) S-(1-methylpropyl) N-methoxymethylcarbonyl N,N'-dimethyl phosphorodiamidothioate N-(4-Bromophenylthiocarbonyl) N,N'-dimethyl N'-(methylthiomethyl) S-propyl phosphorodiamidodithioate N-Hydrogenthiocarbonyl N,N'-dimethyl N'-(phenylthiomethyl) S-propyl phosphorodiamidodithioate N'-Methoxymethyl N,N'-dimethyl N-methylcarbonyl S-[1-methylpropyl) phosphorodiamidothioate
N,N'-Diethyl N'-hexyloxymethyl S-pentyl N-phenylcarbonyl phosphorodiamidothioate
N-Chloroethylcarbonyl N'-ethoxymethyl S-ethyl N,N'-dimethyl phosphorodiamidothioate
N-Hydrogenthiocarbonyl N'-methoxymethyl N,N'-dimethyl S-(2-methylpropyl) phosphorodiamidothioate
S-Butyl N,N'-diethyl N-ethylcarbonyl N'-phenoxymethyl phosphorodiamidodithioate
S-Hexyl N-hexylcarbonyl N'-methoxyethyl N,N'-diethyl phosphorodiamidothioate
N'-Methoxymethyl N,N'-dimethyl N-methylthiocarbonyl S-pentyl phosphorodiamidothioate
N'-Ethoxymethyl N,N',S-triethyl N-ethylcarbonyl phosphorodiamidothioate
N'-Methoxymethyl N,N'-dimethyl S-(1-methylpropyl) N-(2-propenylcarbonyl) phosphorodiamidothioate
N-(3-Hexynyl) N'-methoxyethyl N,N'-dimethyl S propyl phosphorodiamidothioate
N,N'-bis-Hydrogencarbonyl N,N'-dimethyl S-propyl phosphorodiamidothioate
S-Ethyl N-hydrogencarbonyl N'-methylcarbonyl N,N'-dimethyl phosphorodiamidothioate
N,N'-bis-Hexylcarbonyl N,N'-dimethyl S-(1-methylpropyl) phosphorodiamidothioate
N-Cyclopropylcarbonyl N,N'-diethyl S-(2-methylethyl) N'-trifluoromethylcarbonyl phosphorodiamidothioate
N-Cyclohexylcarbonyl N,N'-dimethyl S-pentyl N'-phenylcarbonyl phosphorodiamidothioate
N-(3-Hexynylcarbonyl) N,N'-dimethyl S-(1-methylpropyl N'-(2-propenyl) phosphorodiamidothioate
N-Hydrogenthiocarbonyl N,N'-dimethyl S-(2-methylbutyl) N'-methylthiocarbonyl phosphorodiamidothioate
N-(4-Bromophenylcarbonyl) N'-hydrogenthiocarbonyl N,N'-dimethyl S-(1-methylpropyl) phosphorodiamidothioate
N-Butylcarbonyl S-hexyl N'-methoxymethylcarbonyl N,N'-dimethyl phorphorodiamidothioate
N-Benzylcarbonyl S-ethyl N,N'-dimethyl N'-propylthiocarbonyl phosphorodiamidodithioate The compounds of the invention can be synthesized as is described and outlined below.

N'-Thio substituted diamidates V are prepared by reaction of an N-acyl phosphorodiamidothioate III with a sulfenyl chloride IV in the presence of an acid scavenger and a solvent.

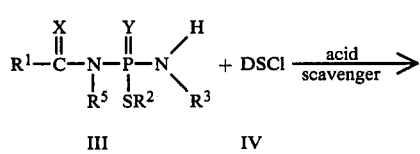

where D=R⁶ or

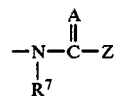

N'-Sulfonyl substituted compounds VI are prepared by a sequential reaction of an N-acyl phosphorodiamidate III with n butyllithium and a sulfonyl halide.

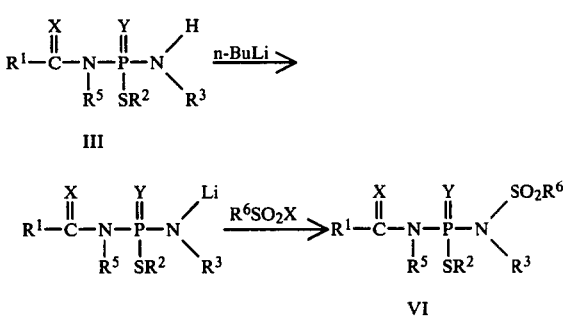

Alternatively, reaction of a sodium salt of a sulfonamide with a phosphorodichloridothioate followed by an alkyl amine gives the sulfonyl diamidate VII. Treatment of VII with n-butyllithium then an anhydride or acid halide produces VI.

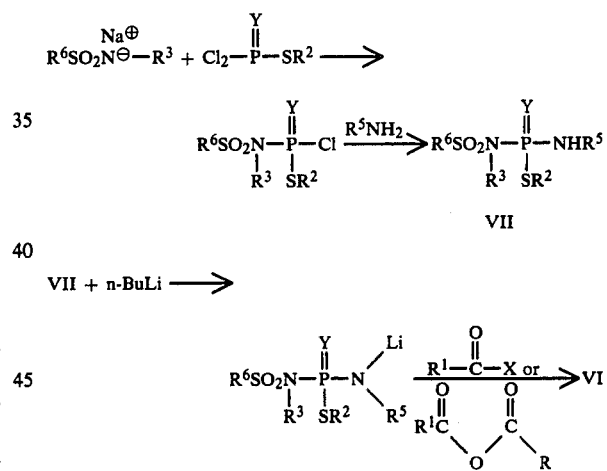

N'-Oxalate (IX) and N'-formate (X) derivatives were prepared by reaction of lithium salt VIII with the appropriate acid halide.

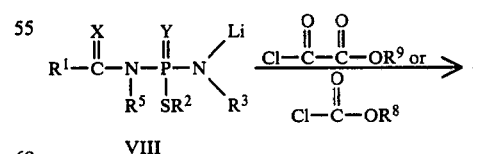

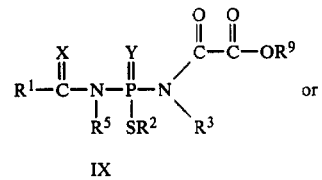

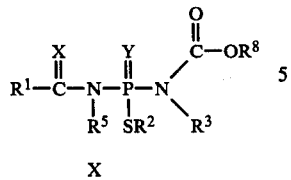

X

N'-Sulfonyl or acyl ureas XI are prepared by reacting an N-acyl phosphorodiamidothioate III with an appropriate sulfonyl- or acyl isocyanate.

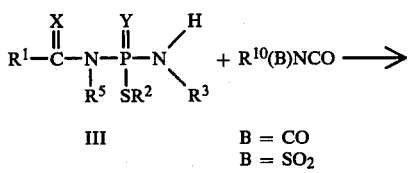

III   B = CO
      B = SO₂

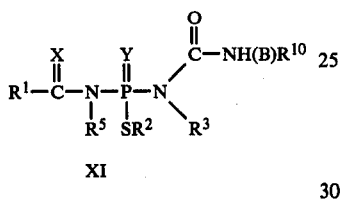

XI

N'-Carbamoyl diamidates XII are prepared by reacting lithium salt VIII with a carbamoyl chloride.

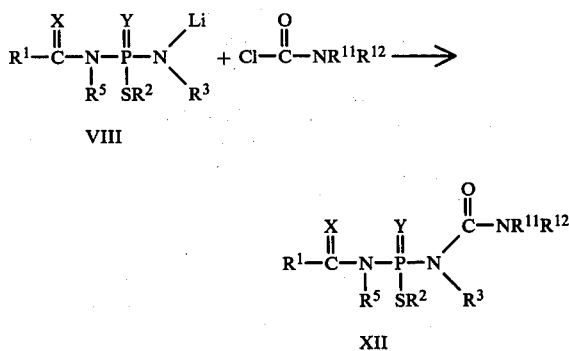

Alternatively, ureas XII can be prepared by sequentially reacting an N-acyl phosphorodiamidothioate III with phosgene and an acid scavenger followed by the appropriate amine and an acid scavenger.

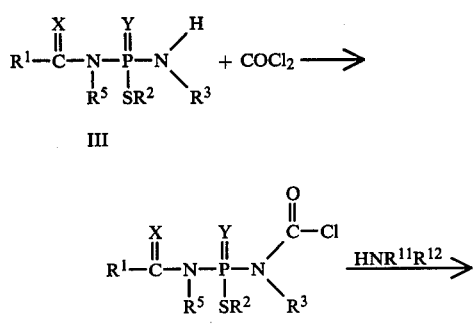

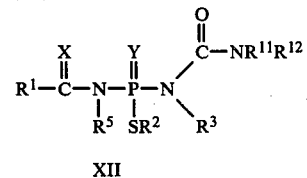

XII

N'-Thioalkyl phosphorodiamidothioate derivatives XIII are prepared by reacting an N-acyl phosphorodiamidothioate III with an appropriate haloalkyl sulfur compound.

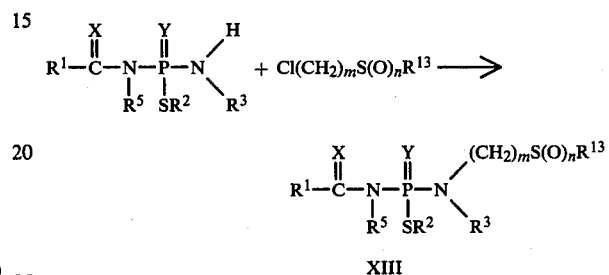

XIII

N,N'-Diacyl diamidates XIV are prepared by reacting lithium salt VIII with an appropriate acid chloride or anhydride.

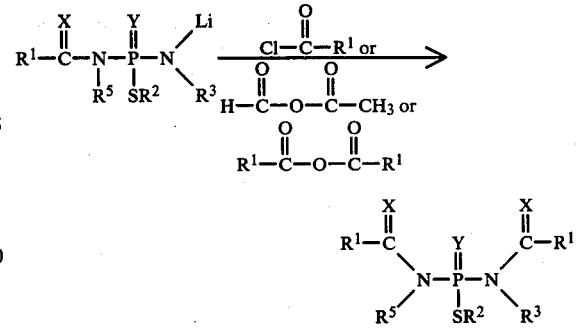

XIV

The compounds of the invention are useful for the protection of plants and animals, including mammals, from the ravages of harmful and annoying pests. These compounds are particularly effective against arthropods (in varying stages of development) and are especially effective against members of the Class Arachnoidea, which includes the Order Acarina, as represented by mites and ticks, and the Class Insecta, the insects. Among the arthropods which are effectively controlled by the compounds of the present invention are the chewing insects, e.g., the southern armyworm (*Spodoptera eridania*), mites, e.g., the two-spotted spider mite (*Tetranychus urticae*) and others.

The compounds of this invention are also active as fungicides.

Furthermore, compounds of this invention possess nematocidal activity. Among the nematodes which are effectively controlled by the compounds of the present invention are soil nematodes, typified by the southern root knot nematode (*Meloidogyne incognita*).

Generally, control of pests is achieved in accordance with this invention by application of the compounds in pesticidally effective amounts (e.g., arthropodicidally effective amounts) either directly to the pests to be controlled or to the loci to be freed of or protected from attack by such pests. Plant protection loci may be defined as the aerial and subterranean portions of plants or propagative subunits and their immediate or future ornamental crops and stored products thereof represent plant protection loci. Treatment with compounds of this invention of domestic animals, and their immediate environs similarly constitute representative loci for protection against various annoying ectoparasitic or endoparasitic Acarina (Acari) and Insecta. Many of the below formulations can be utilized on animals in the control of parasites. Thus, the compounds can be deposited on or in the soil, plants, insects, man-made structures, or other substrates as deposits, coatings, etc. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, inhibition, reduction in number or any combination thereof.

The term "pest" as employed in the specification and claims of this application refers to fungi, nematodes and various arthropods especially insects and acarids.

The phosphorodiamidothioates of this invention possess general utility as arthropodicites, particularly as against members of the class Arachnoidea, which includes the order Acarina, as represented by mites and ticks, and Insecta, the insects. Certain compounds of this invention are also active as nematocides and fungicides, particularly fungicides.

For use as pesticides, the compounds of this invention can be used as solutions in organic solvents or formulations. For example, they can be formulated as wettable powders, emulsifiable concentrates, dusts, granular formulations or flowable emulsifiable concentrates. In such formulations, the phosphorodiamidothioates are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual".

The phosphorodiamidothioates can be taken up or mixed with a finely particled solid carrier, as for example, clays, inorganic silicates, carbonates, and silicas. Organic carriers can also be employed. Dust concentrates are commonly made wherein phosphorodiamidothioates are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The phosphorodiamidothioates are usually present in the range of about 10 to about 35% by weight and surfactants from about 0.5 to about 10% by weight.

One convenient method for preparing a solid formulation is to impregnate the phosphorodiamidothioate onto the solid carrier by means of a volatile solvent such as acetone. In this manner, adjuvants, such as activators, adhesives, plant nutrients, synergists and various surfactants can also be incorporated.

Emulsifiable concentrate formulations can be prepared by dissolving the phosphorodiamidothioate of this inventon in an agronomically acceptable organic solvent and adding a solvent-soluble emulsifying agent. Suitable solvents are usually water-immiscible "Detergents and Emulsifiers Annual".

The phosphorodiamidothioates can be taken up or mixed with a finely particled solid carrier, as for example, clays, inorganic silicates, carbonates, and silicas. Organic carriers can also be employed. Dust concentrates are commonly made wherein phosphorodiamidothioates are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The phosphorodiamidothioates are usually present in the range of about 10 to about 35% by weight and surfactants from about 0.5 to about 10% by weight.

One convenient method for preparing a solid formulation is to impregnate the phosphorodiamidothioate onto the solid carrier by means of a volatile solvent such as acetone. In this manner, adjuvants, such as activators, adhesives, plant nutrients, synergists and various surfactants can also be incorporated.

Emulsifiable concentrate formulations can be prepared by dissolving the phosphorodiamidothioate of this invention in an agronomically acceptable organic solvent and adding a solvent-soluble emulsifying agent. Suitable solvents are usually water-immiscible and can be found in the hydrocarbon, ketone, ester, alcohol and amide groups of organic solvents. Mixtures of solvents are commonly employed. The surfactants useful as emulsifying agents can constitute about 0.5 to about 10% by weight of emulsifiable concentrate and can be anionic, cationic or non-ionic in character. The concentration of the active ingredients can vary from about 20 to about 50%.

For use as pesticidal agents, these compounds should be applied in an effective amount sufficient to exert the desired pesticidal activity by techniques well known in the art. Usually, this will involve the application of the phosphorodiamidothioate to the loci to be protected from or freed of pests in an effective amount when incorporated in an agronomically acceptable carrier. However, in certain situations, it may be desirable and advantageous to apply the compounds directly onto the loci to be protected from or freed of pests without the benefit of any substantial amount of carrier. This is a particularly effective method when the physiccal nature of the toxicants is such as to permit what is known as "low-volume" application, that is, when the compounds are in liquid form or substantially soluble in higher boiling solvents.

The application rate will, of course, vary depending upon the purpose for such application, the phosphorodiamidothioate being utilized, the frequency of dissemination and the like.

By "agronomically acceptable carrier" is meant any substance which can be utilized to dissolve, disperse, or diffuse the chemical incorporated therein without impairing the effectiveness of the toxic agent and which does no permanent damage to such environment as soil, equipment and agronomic crops.

For use as insecticides and acaricdes, dilute sprays can be applied at concentratons of about 0.01 to about 20 pounds of the phosphorodiamidothioate ingredient per 100 gallons of spray. They are usually applied at about 0.1 to about 5 pounds per 100 gallons. In more concentrated sprays, the active ingredient is increased by a factor of about 2 to 12. With dilute sprays, applications are usually made to the plants until run off is achieved, whereas with more concentrated low-volume sprays, the materials are applied as mists.

For use as a fungicide, the compounds of this invention can be applied as fungicidal sprays by methods commonly employed, such as, conventional high-gallonage hydraulic sprays, low-gallonage sprays, airblast sprays, aerial sprays and dusts. The dilution and rate of application will depend upon the type of equipment employed, the method of application and diseases to be controlled, but the preferred effective amount is usually about 0.1 lb. to about 50 lbs. per acre of the active ingredient.

As a fungicidal seed protectant, the amount of toxicant coated on the seed is usually at a dosage rate of about 0.1 to about 20 ounces per hundred pounds of seed. As a soil fungicide the chemical can be incorporated in the soil or applied to the surface usually at a rate of about 0.1 to about 50 lbs. per acre. As a foliar fungicide, the toxicant is usually applied to growing plants at a rate of about 0.25 to about 10 lbs. per acre.

For use as a nematocide, systemic agent, or as a soil insecticide, the phosphorodiamidothioates can be applied as a solid formulation, preferably a granular formulation or as a diluted liquid preparation, by broadcasting, sidedressing soil incorporation or seed treatment.

The composition can also be added to transplant or irrigation water or to units employed in propagation, such as seeds, tubers, roots, seedlings, etc., so as to disinfect and/or provide residual protection from nematodes, soil insects (and mits) and via systemic uptake foliar pests. The application rate can be from about 0.5 to about 50 pounds per acre; however, higher rates can also be used. The preferred rate is from about 1 to about 25 pounds per acre. For soil incorporation, the compounds of this invention can be mixed with the soil or other growth medium at a rate of about 1 to about 100 ppm of active ingredient.

The compounds of this invention can be utilized as the sole pesticidal agents or they can be employed in conjunction with other bacteridices, fungicides, herbicides, insecticides, acaricides, namtocides and comparable pesticides.

The following examples illustrate but a few embodiments of the invention and are not to be construed as limiting in scope. All parts and percentages are by weight unless otherwise indicated.

EXPERIMENTAL SECTION

Example 1: N-Hydrogencarbonyl N,N'-dimethyl N'-(4-methylphenylthio) S-(1-methylpropyl) phosphorodiamidothioate.

Sulfuryl chloride (4.00 g, 0.03 moles) is added to an ice-cooled solution of p-tolyl disulfide (7.38 g, 0.03 moles) in 50 ml of toluene. After stirring 10 minutes at ice bath temperature, the resulting sulfenyl chloride is added dropwise to an ice-cooled solution of triethylamine (5.43 g, 0.054 moles) and N-hydrogencarbonyl N,N'-dimethyl S-(1-methylpropyl) phosphorodiamidothioate in 50 ml of dimethyl formamide. After stirring two hours at room temperature, the reaction was diluted with 100 ml of water and extracted with 2×250 ml of ether. The ether layers were dried over 4 A molecular sieves and evaporated. Purification by preparative HPLC using a PrepPak 500 silica gel column and a mobile phase of 60/40 ethyl acetate/isooctane gave 2.5 g of desired product.

The reaction can also be run in methylene chloride substituting pyridine for triethylamine.

The following compounds were prepared using a procedure substantially the same as in Example 61 analogous to preceding page.

Example 2: N-Hydrogencarbonyl N'-[(methoxycarbonyl)thio] N,N'-dimethyl S-(1-methylpropyl) phosphorodiamidothioate Example 3: N-Hydrogencarbonyl N,N'-dimethyl S-(1-methylpropyl) N'-trichloromethylthio phosphorodiamidothioate.

Example 4: N-Hydrogencarbonyl N,N'-dimethyl S-(1-methylpropyl) N'-[(propoxycarbonyl)methylaminothio] phosphorodiamidothioate.

Sulfur dichloride (7.23 g, 0.07 moles) is added dropwise to N-methylpropyl carbamate (6.32 g, 0.054 moles) in 50 ml of methylene chloride. Pyridine (4.27 g, 0.054 moles) is added and the reaction is stirred one hour at room temperature. The resulting solution of sulfenyl chloride is diluted with 200 ml of ether, filtered to remove the pyridine hydrochloride, and concentrated by vacuum evaporation. The sulfenyl chloride is added dropwise to a solution of pyridine (4.27 g, 0.054 moles) and N-hydrogencarbonyl N,N'-dimethyl S-(1-methylpropyl) phosphorodiamidothioate (12.1 g, 0.054 moles) in 100 ml of methylene chloride. The solution was stirred 2 hours at room temperature, diluted with 200 ml of ether, filtered to remove the pyridine hydrochloride, and evaporated to yield 20 g of oil. Purification by preparative HPLC gave 1 g. of product.

The following compounds were prepared by substantially the same procedure as in Example 4:

Example 5: N'[(Ethoxycarbonyl)(methyl)aminothio]N-hydrogencarbonyl N,N'-dimethyl S-(1-methylpropyl) phosphorodiamidothioate.

Example 6: N'-[(Decyloxycarbonyl)(methyl)aminothio]N-hydrogencarbonyl N,N'-dimethyl S-(1-methylpropyl) phosphorodiamidothioate.

Example 7: N-Hydrogencarbonyl N,N'-dimethyl N'-[(1-methylethoxy)carbonyl ] (methyl)aminothio]] S-(1-methylpropyl) phosphorodiamidothioate.

Example 8: N-Hydrogencarbonyl N'-[(methoxycarbonyl) (methyl)aminothio] N,N'-dimethyl S-(1-methylpropyl) phosphorodiamidothioate.

Example 8(a) N'-Carbofuranthio N-hydrogencarbonyl N,N'-dimethyl S-(1-methylpropyl) phosphorodiamidothioate.

Example 8(b) [N'-(Ethylthiocarbonyl)(methyl)aminothio] N-hydrogencarbonyl N,N'-dimethyl S-(1-methylpropyl) phosphorodiamidothioate.

Example 8(c) [N'-(Benzyloxycarbonyl)(methyl)aminothio] N-hydrogencarbonyl N,N'-dimethyl S-(1-methypropyl) phosphorodiamidothioate.

Example 8(d) N-Hydrogencarbonyl N-[(methoxycarbonyl)(1-methylethyl)aminothio] N,N'-dimethyl S-(1-methylpropyl) phosphorodiamidothioate.

Example 8(e) N'[(Benzyl)methylaminothio] N-hydrogencarbonyl N,N'-dimethyl S-(1-methylpropyl) phosphorodiamidothioate.

Example 9: N-Hydrogencarbonyl N'-methanesulfonyl N,N'-dimethyl S-(1-methylpropyl) phosphorodiamidothioate.

A. N-methyl methanesulfonamide (39.8 g, 0.36 moles) is added dropwise to a suspension of sodium hydride (17.5 g of 50% dispersion in mineral oil, 0.365 moles) in tetrahydrofuran (THF). The reaction is stirred overnight at room temperature, the reaction is cooled to −40° with a dry ice acetone bath, and S-sec-butyl phosphorodichloridothioate is added all at once. The reaction is stirred 4 hours at room temperature, cooled with an ice bath, and a solution of methylamine (11.31 g, 0.365 moles) and triethylamine (36.9 g, 0.365 moles) in 100 ml of THF is added dropwise. The reaction is filtered and evaporated under vacuum, giving 100 grams of N'-methanesulfonyl N,N'-dimethyl S-(1-methylpropyl) phosphorodiamidothioate.

B. n-Butyllithium (0.033 moles) is added dropwise to a solution of the product formed in part A (9.04 g, 0.033 moles) in 200 ml of THF, cooled to −40° C. Mixed formic-acetic anhydride (3.43 g, 0.033 moles) is added at −40° C. The solution is stirred at room temperature for one-half hour, diluted with 200 ml of ether, filtered, and evaporated, giving 10 g of oil. Purification by preparative HPLC gave 2.1 g of product.

The following compounds were prepared by substantially the same procedure as in Example 4:

Example 10: N'-Methanesulfonyl N,N'-dimethyl N-methylcarbonyl S-(1-methylpropyl) phosphorodiamidothioate.

Example 11: N'-Methanesulfonyl N,N'-dimethyl S-(1-methylpropyl) N-phenylcarbonyl phosphorodiamidothioate.

Example 12: N'-Butylsulfonyl N-hydrogencarbonyl N,N'-dimethyl S-(1-methylpropyl) phosphorodiamidothioate.

Example 13: N-Hydrogencarbonyl N,N'-dimethyl S-(1-methylpropyl) N'-trifluoromethanesulfonyl phosphorodiamidothioate.

n-Butyllithium (0.0296 moles) is added to a solution of N-hydrogencarbonyl N,N'-dimethyl S-(1-methylpropyl) phosphorodiamidothioate (6.63 g, 0.0296 moles) in 100 ml of THF at −40° C. Trifluoromethanesulfonyl chloride (5 g, 0.0296 moles) is added over 2 minutes, the reaction is stirred 5 minutes, diluted with 100 ml of ether, filtered, and evaporated to give 5.2 g of oil. Purification by HPLC gave the product.

The following compounds were prepared by substantially the same procedure as in Example 13.

Example 14: N-Hydrogencarbonyl N,N'-dimethyl S-(1-methylpropyl) N'-phenylsulfonyl phosphorodiamidothioate.

Example 15: N-Hydrogencarbonyl N'-(methoxycarbonyl)carbonyl N,N'-dimethyl S-(1-methylpropyl) phosphorodiamidothioate.

Example 16: N-Hydrogencarbonyl N'-[(1-methylethoxy)carbonyl]carbonyl N,N'-dimethyl S-(1-methylpropyl) phosphorodiamidothioate.

Example 16(a) N-Hydrogencarbonyl N'-(methoxycarbonyl)carbonyl N,N'-dimethyl S-(1-methylpropyl) phosphorodiamidothioate Example 16(b) N'-(Ethoxycarbonyl)carbonyl N-hydrogencarbonyl N,N'-dimethyl S-(1-methylporpyl) phosphorodiamidothioate Example 16(c) N-Hydrogencarbonyl N'-[(propylthio)carbonyl]carbonyl N,N'-dimethyl S-(1-methylpropyl) phosphorodiamidothioate Example 16(d) N'-(Benzyloxycarbonyl)carbonyl N-hydrogencarbonyl N,N'-dimethyl S-(1-methylpropyl) phosphorodiamidothioate Example 16(e) N'-(2-Chloroethoxycarbonyl)carbonyl N-hydrogencarbonyl N,N'-dimethyl S-(1-methylpropyl) phosphorodiamidothioate Example 16(f) N-Hydrogencarbonyl N,N'-dimethyl N'-(1,1-dimethylethoxy carbonyl)carbonyl S-(1-methylpropyl) phosphorodiamidothioate Example 16(g) N-Hydrogencarbonyl N'-(2-methoxyethoxy carbonyl)carbonyl N,N'-dimethyl S-(1-methylpropyl) phosphorodiamidothioate Example 16(h) N'-(Cyclohexyloxycarbonyl)carbonyl) N-hydrogencarbonyl N,N'-dimethyl S-(1-methyl propyl) phosphorodiamidothioate Example 16(i) N-Hydrogencarbonyl N,N'-dimethyl N'-[(1-methylethyliminooxy)carbonyl]carbonyl) S-(1-methylpropyl) phosphorodiamidothioate Example 16(j) N-Hydrogencarbonyl N'-(4-methoxyphenoxycarbonyl)-carbonyl N,N'-dimethyl S-(1-methylpropyl) phosphorodiamidothioate Example 16(k) N-Hydrogencarbonyl N,N'-dimethyl S-(1-methylpropyl) N'-(phenoxy carbonyl)carbonyl phosphorodiamidothioate Example 17: N-Hydrogencarbonyl N,N'-dimethyl S-(1-methylpropyl) N'-[(phenylmethoxy)carbonyl] phosphorodiamidothioate.

Example 18: N-Hydrogencarbonyl N,N'-dimethyl S-(1-methylpropyl) N'-(2-trichloroethoxycarbonyl) phosphorodiamidothioate.

Example 19: N'-[(Ethoxy)carbonyl] N'-hydrogencarbonyl N,N'-dimethyl S-(1-methylpropyl) phosphorodiamidothioate.

Example 20: N'-[(Ethylidenoxy)carbonyl] N'-hydrogencarbonyl N,N'-dimethyl S-(1-methylpropyl) phosphorodiamidothioate.

Triethylamine (2.22 g, 0.022 moles) is added to a solution of vinyl chloroformate (2.34 g, 0.022 moles) and N-hydrogencarbonyl N,N'-dimethyl S-(1-methylpropyl) phosphorodiamidothioate (5 g, 0.022 moles) in 50 ml of THF at room temperature. The reaction was filtered and evaporated to give 6.5 g of oil. Purification by preparative HPLC gave 2 g of product.

Example 21: N,N'-bis-Hydrogencarbonyl N,N'-dimethyl S-(1-methylpropyl phosphorodiamidothioate.

The components of a 50 g sample of impure N-hydrogencarbonyl N,N'-dimethyl S-(1-methylpropyl) phosphorodiamidothioate were isolated by HPLC. About 300 mg of bis-hydrogencarbonyl product were found.

Example 22: N-Hydrogencarbonyl N,N'-dimethyl N'-trifluoromethylcarbonyl S-(1-methylpropyl) phosphorodiamidothioate.

Trifluoroacetic anhydride (25.2 g, 0.12 moles) and N-hydrogencarbonyl N,N'-dimethyl S-(1-methylpropyl) phosphorodiamidothioate (22.5 g, 0.1 moles) are stirred 16 hours at room temperature, 8 hours at 30° C., and 20 minutes at 150° C. The resulting mixture is evaporated under vacuum and purified by chromatography on Biosil A and preparative HPLC to give 3 g of product.

Example 23: N-Hydrogencarbonyl N,N'-dimethyl S-(1-methylpropyl) N'-methylthiomethyl phosphorodiamidothioate.

Chloromethyl methyl sulfide (6.47 g, 0.067 moles) and N-hydrogencarbonyl N,N'-dimethyl S-(1-methylpropyl) phosphorodiamidothioate (15 g, 0.067 moles) were stirred 6 days in 50 ml of dimethyl formamide. The solution was diluted with 100 ml of ether and extracted twice with 100 ml of water. The ether solution was dried with 4° molecular sieves, filtered, and evaporated to give 8 g of oil. Purification by preparative HPLC gave 1.3 g of product.

Example 24: N-Hydrogencarbonyl N,N'-dimethyl N'-[(4-methylphenyl)sulfonylaminocarbonyl] S-(1-methylpropyl) phosphorodiamidothioate.

p-Tolylisocyanate (8.87 g, 0.045 moles) and N-hydrogencarbonyl N,N'-dimethyl S-(1-methylpropyl) phosphorodiamidothioate (10.0 g, 0.045 moles) were stirred in 10 ml of THF for 16 hours at room temperature. The solvent was evaporated, leaving 20 g of oil. Purification by HPLC gave 2.4 g of product.

The following compounds were prepared by substantially the same procedure as in Example 4:

Example 25: N-Hydrogencarbonyl N,N'-dimethyl S-(1-methylpropyl) N'-(phenylsulfonylaminocarbonyl) phosphorodiamidothioate.

Example 26: N-Hydrogencarbonyl N,N'-dimethyl S-(1-methylpropyl) N'-(trichloromethyl) carbonylaminocarbonyl phosphorodiamidothioate.

Example 27: N-Hydrogencarbonyl N,N'-dimethyl S-(1-methylpropyl) N'-phenylcarbonylaminocarbonyl phosphorodiamidothioate.

Example 28: N-Hydrogencarbonyl N,N'-dimethyl N'-(methylaminocarbonyl) S-(1-methylpropyl) phosphorodiamidothioate.

A solution of N-hydrogencarbonyl N,N'-dimethyl S-(1-methylpropyl) phosphorodiamidothioate (20 g, 0.089 moles) and pyridine (7.03 g, 0.09 moles) is added to an ice-cooled solution of phosgene (8.99 g, 0.089 moles) in toluene. A solution of methylamine (5.51 g, 0.178 moles) in 100 ml of THF is added and the reaction is stirred 2 hours at ambient temperature. The reaction is filtered and evaporated. Purification by HPLC gave 2 g of product.

Table I--NMR Data

Numbers are expressed in PPM, relative to tetramethylsilane.

Example 1 9.23 (s, 1H, CO$\underline{H}$); 7.15 (q, 4H, arom); 3.30 (m, 1H, SC$\underline{H}$); 3.08 (d, 3H, NC$\underline{H}_3$); 2.8 (d, 3H, NC$\underline{H}_3$); 2.25 (s, 3H, S-C$_6$H$_4$-C$\underline{H}_3$); 1.62 (m, 2H, SCHC$\underline{H}_2$); 1.36 (d, d, 3H, SCH(C$\underline{H}_3$); 0.94 (t, 3H, SCHC$\underline{H}_2$CH$_3$).

Example 2 9.00 (s, 1H, CO$\underline{H}$); 3.85 (s, 3H, OC$\underline{H}_3$); 3.30 (m, 1H, SC$\underline{H}$); 3.20 (d, 3H, NC$\underline{H}_3$); 2.95 (d, 3H, NC$\underline{H}$); 1.62 (m, 2H, SCHC$\underline{H}_2$); 1.42 [d, d, 3H, SC$\underline{H}$(CH$_3$)]; 1.0 (t, 3H, SCHC$\underline{H}_2$CH$_3$).

Example 3 8.83 (s, 1H, CO$\underline{H}$); 3.45 (d, 3H, NC$\underline{H}_3$); 3.45 (m, 1H, SC$\underline{H}$); 2.94 (d, 3H, NC$\underline{H}_3$); 1.75 (m, 2H, SCHC$\underline{H}_2$); 1.42 [[d, of d, 3H, SCH(C$\underline{H}_3$)]; 1.0 (m, 3H, SCHC$\underline{H}_2$CH$_3$).

Example 4 8.93 (s, 1H, CO$\underline{H}$); 4.05 (t, 2H, OC$\underline{H}_2$); 3.35 (s, 3H, NC$\underline{H}_3$); 3.22 (d, 3H, NC$\underline{H}_3$); 3.22 (m, 1H, SC$\underline{H}$); 2.8 (d, 3H, NC$\underline{H}_3$); 1.75 (m, 2H, SCHC$\underline{H}_2$); 1.75 (m, 2H, OCH$_2$C$\underline{H}_2$); 1.42 [(d, 3H, SCH(C$\underline{H}_3$)]; 0.95 (m, 6H, OCH$_2$C$\underline{H}_2$CH$_3$); and SCHCH$_2$C$\underline{H}_3$).

Example 5 8.97 (s, 1H, CO$\underline{H}$); 4.26 (q, 2H, OC$\underline{H}_2$); 2.40 (s, 3H, NC$\underline{H}_3$); 3.28 (d, 3H, NC$\underline{H}_3$); 2.82 (d, 3H, NC$\underline{H}_3$); 1.72 (m, 2H, SCHC$\underline{H}_2$); 1.50 [(d, 3H, SC$\underline{H}$(CH$_3$)], 1.38 (t, 3H, OCH$_2$C$\underline{H}_3$); 1.01 (m, 3H, SCHC$\underline{H}_2$CH$_3$).

Example 6 9.03 (s, 1H, CO$\underline{H}$); 4.02 (q, 2H, OC$\underline{H}_2$); 3.38 (s, 3H, NC$\underline{H}_3$); 3.26 (d, 3H, NC$\underline{H}_3$); 3.26 (m, 1H, SC$\underline{H}$); 2.90 (t, 3H, NC$\underline{H}_3$); 2.90 (m, 2H, OCH$_2$C$\underline{H}_2$); 1.82 (m, 2H, SCHC$\underline{H}_2$); 1.35 [m, 23H, (C$\underline{H}_2$)$_7$C$\underline{H}_3$, SCH(C$\underline{H}_3$)CH$_2$CH$_3$].

Example 7 9.03 (s, 1H, CO$\underline{H}$); 4.95 (m, 1H, OC$\underline{H}$); 3.35 (s, 3H, NC$\underline{H}_3$); 3.25 (d, 3H, NC$\underline{H}_3$); 3.25 (m, 1H, SC$\underline{H}$); 2.82 (d, 3H, NC$\underline{H}_3$); 1.72 (m, 2H, SCHC$\underline{H}_2$); 1.42 [(d, 3H, SCH(C$\underline{H}_3$)]; 1.36 [(d, 6H, OCH(C$\underline{H}_3$)$_2$]; 1.0 (m, 3H, SCHC$\underline{H}_2$CH$_3$).

Example 8 9.03 (s, 1H, CO$\underline{H}$); 3.82 (s, 3H, OC$\underline{H}_3$); 3.35 (s, 3H, NC$\underline{H}_3$); 3.25 (d, 3H, NC$\underline{H}_3$); 3.25 (m, 1H, SC$\underline{H}$); 2.82 (d, 3H, NC$\underline{H}_3$); 1.72 (m, 2H, SCHC$\underline{H}_2$); 1.42 [d, 3H, SCH(C$\underline{H}_3$)]; 1.0 (m, 3H, SCH$_2$CH$_2$C$\underline{H}_3$).

Example 8a 9.00 (s, 1H, CO$\underline{H}$); 6.84 (m, 3H, C$_6$H$_3$); 3.50 (s, 3H, NC$\underline{H}_3$); 3.35 (, 1H, SC$\underline{H}$); 3.31 (d, 3H, NC$\underline{H}_3$); 3.02 (s, 2H, C$\underline{H}_2$); 2.82 (d, 3H, NC$\underline{H}_3$); 1.65 (m, 2H, SCHC$\underline{H}_2$); 1.40 [s, 6H, (C$\underline{H}_3$)$_2$]1.40 [m, 6H, SCH(C$\underline{H}_3$)CH$_2$CH$_3$]

Example 8b 9.00 (s, 1H, CO$\underline{H}$); 3.10 (m, 12H, SC$\underline{H}$, NC$\underline{H}_3$); NC$\underline{H}_3$, NC$\underline{H}_3$, SC$\underline{H}_2$CH$_3$); 1.75(m, 2$\underline{H}$, SCHC$\underline{H}_2$); 1.00 (m, 9$\underline{H}$, SCH(C$\underline{H}_3$), SCHSC$_2$C$\underline{H}_3$)

Example 8c 9.00 (s, 1H, CO$\underline{H}$); 7.45 (s, 5H, C$_6$H$_5$); 5.18 (d, 2H, C$\underline{H}_2$ C$_6$H$_5$); 3.38 (s, 3H, NC$\underline{H}_3$); 3.42 (s, 1H, SC$\underline{H}$); 3.28 (d, 3H, NC$\underline{H}_3$); 2.82 (d, 3H, NC$\underline{H}_3$); 1.68 (m, 2H, SCHC$\underline{H}_2$); 1.40 [m, 3H, SCH(C$\underline{H}_3$)]; 1.00 (m, 3H, SCHC$\underline{H}_2$CH$_3$)

Example 8d 9.00 (a, 1H, CO$\underline{H}$); 4.60 [m, 1H, CH(CH$_3$)$_2$]3.90 (s, 3H, NC$\underline{H}_3$); 3.32 (d, 3H, NC$\underline{H}_3$); 2.90 (d, 3H, NC$\underline{H}_3$); 1.62 (m, 2H, SCHC$\underline{H}_2$); 1.50[m, 3H, SCH(C$\underline{H}_3$)]; 1.40 [d, 6H, CH(C$\underline{H}_3$)$_2$]1.00 (m, 3H, SCHC$\underline{H}_2$CH$_3$)

Example 8e 9.00 (s, 1H, CO$\underline{H}$); 7.38 (s, 5H, C$_6$H$_4$); 4.40 (s, 2H, C$_6$H$_4$C$\underline{H}_2$); 3.30 (d, 3H, NC$\underline{H}_3$); 2.85 (s, 3H, NC$\underline{H}_3$); 2.85 (d, 3H, NC$\underline{H}_3$); 1.70 (m, 2H, SCHC$\underline{H}_2$); 1.50 [m, 3H, SCH(C$\underline{H}_3$)]1.00 (t, 3H, SCHC$\underline{H}_2$CH$_3$)

Example 9 9.03 (s, 1H, CO$\underline{H}$); 3.30 (d, 3H, NC$\underline{H}_3$); 3.30 (m, 1H, SC$\underline{H}$); 3.22 (d, 3H, NC$\underline{H}_3$); 1.72 (m, 2H, SCHC$\underline{H}_2$); 1.5 [d of d, 3H, SCH(C$\underline{H}_3$)]; 1.0 (m, 3H, SCHC$\underline{H}_2$CH$_3$).

Example 10 3.8 (m, 1H, SC$\underline{H}$); 3.38 (d, 3H, NC$\underline{H}_3$); 3.21 (s, 3H, CH$_3$SO$_2$); 3.20 (d, 3H, NC$\underline{H}_3$); 1.78 (m, 2H, SCHC$\underline{H}_2$); 1.50 [d of d, 3H, SCH(C$\underline{H}_3$)]; 1.0 (m, 3H, SCHC$\underline{H}_2$CH$_3$).

Example 11 7.5 (s, 5H, C$_6$H$_5$); 3.75 (m, 1H, SC$\underline{H}$); 3.42 (d, 3H, NC$\underline{H}_3$); 3.30 (s, 3H, CH$_3$SO$_2$); 3.18 (d, 3H, NC$\underline{H}_3$); 1.82 (m, 2H, SCHC$\underline{H}_2$); 1.50 [d, 3H, SC$\underline{H}$(CH$_3$)]; 1.0 (m, 3H, SCHC$\underline{H}_2$CH$_3$).

Example 12 9.07 (s, 1H, CO$\underline{H}$); 3.75 (m, 1H, SC$\underline{H}$); 3.02 (d, 3H, NC$\underline{H}_3$); 3.01 (m, 2H, SO$_2$C$\underline{H}_2$); 2.90 (d, 3H, NC$\underline{H}_3$); 1.62 (m, 2H, SCHC$\underline{H}_2$); 1.18 [m, 1 OH, SO$_2$CH$_2$(CH$_2$)$_2$CH$_3$, SCHCH$_2$CH$_3$].

Example 13 9.00 (s, 1H, CO$\underline{H}$); 3.35 (m, 1H, SC$\underline{H}$); 3.14 (d, 3H, NC$\underline{H}_3$); 2.90 (d, 3H, NC$\underline{H}_3$); 1.65 (m, 2H, SCHC$\underline{H}_2$); 1.10 [m, 6H, SCH(CH$_3$)CH$_2$CH$_3$].

Example 14 9.03 (s, 1H, CO$\underline{H}$); 7.80 (m, 5H, C$_6$H$_5$); 3.50 (m, 1H, SC$\underline{H}$); 3.18 (d, 3H, NC$\underline{H}_3$); 3.00 (d, 3H, NC$\underline{H}_3$); 1.72 (m, 2H, SCHC$\underline{H}_2$); 1.50 [d, 3H, SC$\underline{H}$(CH$_3$)]; 1.0 (t, 3H, SCHCH$_2$CH$_3$).

Example 15 9.00 (s, 1H, CO$\underline{H}$); 3.80 (m, 1H, SC$\underline{H}$); 3.80 (s, 1H, OC$\underline{H}_3$); 3.08 (d, 3H, NC$\underline{H}_3$); 3.00 (d, 3H, NCH$_3$); 1.72 (d, 2H, SCHCH$_2$); 1.50 [d, 3H, SCH(CH$_3$)]; 1.00 (t, 3H, SCHCH$_2$CH$_3$).

Example 16 9.03 (s, 1H, COH); 5.16 (m, 1H, OCH); 3.65 (m, 1H, SCH); 3.17 (d, 3H, NCH$_3$); 3.00 (d, 3H, NCH$_3$); 1.72 (m, 2H, SCHCH$_2$); 1.50 [d, 3H, SCH(CH$_3$)]; 1.00 (t, 3H, SCHCH$_2$CH$_3$).

Example 16a 9.00 (s, 1H, COH); 4.00 (m, 1H, SCH); 3.90 (s, 3H, OCH$_3$); 3.05 (d, 3H, NCH$_3$); 3.00 (d, 3H, NCH$_3$); 1.65 (m, 2H, SCHCH$_2$); 1.50 [d, 3H, SCH(CH$_3$)]; 1.00 (m, 3H, SCHCH$_2$CH$_3$)

Example 16b 9.00 (s, 1H, COH); 4.40 (l, 2H, OCH$_2$); 3.75 (m, 1H, SCH); 3.10 (d, 3H, NCH$_3$); 3.02 (d, 3H, NCH$_3$); 1.75 (m, 2H, SCHCH$_2$); 1.60 [d, 3H, SCH(CH$_3$)]; 1.40 (t, 3H, OCH$_2$CH$_3$); 1.00 (t, eH, SCHCH$_2$CH$_3$).

Example 16c 9.01 (s, 1H, COH); 3.70 (m, 1H, SCH); 3.32 (d, 3H, NCH$_3$); 3.02 (d, 3H, NCH$_3$); 3.02 (t, 2H, SCH$_2$); 1.72 (m, 4H, SCHCH$_2$, SCH$_2$CH$_2$); 1.00 (t, 6H, SCHCH$_2$CH$_3$); SCH$_2$CH$_2$CH$_3$)

Example 16d 9.01 (s, 1H, COH); 7.40 (s, 5H, C$_6$H$_5$); 5.35 (s, 2H, CH$_2$C$_6$H$_5$); 3.60 (m, 1H, SCH); 3.10 (d, 3H, NCH$_3$); 3.00 (d, 3H, NCH$_3$); 1.72 (m, 2H, SCHSH$_2$); 1.42 [m, 3H, SCH(CH$_3$)]; 1.00 (m, 3H, SCHCH$_2$CH$_3$).

Example 16e 9.00 (s, 1H, COH); 4.60 (t, 2H, CH$_2$Cl); 3.80 (t, 2H, OCH$_2$); 3.65 (m, 1H, SCH); 3.18 (d, 3H, NCH$_3$); 3.15 (d, 3H, NCH$_3$); 1.62 (m, 2H, SCHCH$_2$); 1.50 [d, 3H, SCH(CH$_3$)]1.0 (t, 3H, SCHCH$_2$CH$_3$)

Example 16f 9.00 (s, 1H, COH); 3.60 (m, 1H, SCH); 3.18 (d, 3H, NCH$_3$); 3.05 (d, 3H, NCH$_3$); 1.72 (m, 2H, SCHCH$_2$); 1.60 [s, 9H, (CH$_3$)$_3$]; 1.60 [m, 3H, SCH(CH$_3$)]; 1.00 (t, 3H, SCHCH$_2$CH$_3$).

Example 16g 9.00 (s, 1H, COH); 4.50 (m, 2H, OCH$_2$); 3.80 (m, 2H, CH$_2$OCH$_3$); 3.80 (m, 1H, SCH); 3.48 (s, 3H, OCH$_3$); 3.20 (d, 3H, NCH$_3$); 3.10 (d, 3H, NCH$_3$); 1.75 (m, 2H, SCHCH$_2$); 1.75 [d, 3H, SCH(CH$_3$)]1.00 (t, 3H, SCHCH$_2$CH$_3$)

Example 16h 9.20 (s, 1H, COH); 5.00 (m, 1H, OCH); 3.75 (m, 1H, SCH); 3.18 (d, 3H, NOH$_3$); 3.05 (d, 3H, NCH$_3$); 1.60 [m, 15H, SCHCH$_2$, SCH(CH$_3$), C$_6$H$_{10}$]; 1.02 (t, 3H, SCHCH$_2$CH$_3$)

Example 16i 9.00 (s, 1H, COH); 3.70 (m, 1H, SCH); 3.15 (d, 3H, NCH$_3$); 3.12 (d, 3H, NCH$_3$); 2.10 [d, 6H, (CH$_3$)$_2$]; 1.82 (m, 2H, SCHCH$_2$); 1.50 [d, 3H, SCH(CH$_3$)]1.00 (t, 3H, SCHCH$_2$CH$_3$)

Example 16j 9.00 (s, 1H, COH); 7.05 (m, 4H, C$_6$H$_4$); 3.82 (s, 1H, OCH); 3.80 (m, 1H, SCH); 3.10 (d, 3H, NCH); 3.08 (d, 3H, NCH$_3$); 1.70 (m, 2H, SCHCH$_2$); 1.48 [d, 3H, SCH(CH$_3$)]; 1.00 (t, 3H, SCHCH$_2$CH$_3$)

Example 16k 9.00 (s, 1H, COH); 7.35 (m, 5H, C$_6$H$_5$); 3.80 (m, 1H, SCH); 3.30 (d, 3H, NCH$_3$); 3.28 (d, 3H, NCH$_3$); 1.65 (m, 2H, SCHCH$_2$); 1.50 [d, 3H, SCH(CH$_3$)]; 1.00 (t, 3H, SCHCH$_2$CH$_3$)

Example 17 9.03 (s, 1H, COH); 7.35 (s, 5H, C$_6$H$_5$); 5.18 (s, 1H, CO$_2$CH$_2$); 3.55 (m, 1H, SCH); 3.12 (d, 3H, NCH$_3$); 2.82 (d, 3H, NCH$_3$); 1.72 (m, 2H, SCHCH$_2$); 1.40 [d of d, 3H, SCH(CH$_3$)]; 0.98 (t, 3H, SCHCH$_2$CH$_3$).

Example 18 9.28 (s, 1H, COH); 4.80 (s, 1H, OCH$_2$); 3.50 (m, 1H, SCH); 3.34 (d, 3H, NCH$_3$); 3.00 (d, 3H, NCH$_3$); 1.68 (m, 2H, SCHCH$_2$); 1.47 [d of d, 3H, SCH(CH$_3$)]; 1.00 (t, 3H, SCHCH$_2$CH$_3$).

Example 19 9.00 (s, 1H, COH); 4.20 (q, 2H, OCH$_2$); 3.60 (m, 1H, SCH); 3.10 (d, 3H, NCH$_3$); 2.94 (d, 3H, NCH$_3$); 1.72 (m, 2H, SCHCH$_2$); 1.10 [m, 9H, SCH(CH$_3$)CH$_2$CH$_3$, OCH$_2$CH$_3$].

Example 20 9.03 (s, 1H, COH); 7.05 (m, 1H, C=CH); 4.77 (m, 2H, CH=CH$_2$); 3.6 (m, 1H, SCH); 3.24 (d, 3H, NCH$_3$); 2.96 (d, 3H, NCH$_3$); 1.64 (m, 2H, SCHCH$_2$); 1.45 [d of d, 3H, SCH(CH$_3$)]; 1.00 (t, 3H, SCHCH$_2$CH$_3$).

Example 21 Not available.

Example 22 9.03 (s, 1H, COH); 3.65 (m, 1H, SCH); 3.40 (d, 3H, NCH$_3$); 3.00 (d, 3H, NCH$_3$); 1.80 (m, 2H, SCHCH$_2$); 1.50 [d, 3H, SCH(CH$_3$)]; 1.00 (t, 3H, SCHCH$_2$CH$_3$).

Example 23 9.00 (s, 1H, COH); 4.30 (d, 2H, NCH$_2$S); 3.40 (m, 1H, SCH); 2.95 (d, 3H, NCH$_3$); 2.82 (d, 3H, NCH$_3$); 2.20 (s, 3H, SCH$_3$); 1.72 (m, 2H, SCHCH$_2$); 1.44 [d of d, 3H, SCH(CH$_3$)]; 1.00 (m, 3H, SCHCH$_2$CH$_3$).

Example 24 10.03 (br s, 1H, NHSO$_2$); 9.3 (s, 1H, COH);7.60 (m, 4H, C$_6$H$_4$); 3.60 (m, 1H, SCH); 2.97 (d, 3H, NCH$_3$); 2.80 (d, 3H, NCH$_3$); 2.40 (s, 3H, C$_6$H$_5$CH$_3$); 1.72 (m, 2H, SCHCH$_2$); 1.54 [d of d, 3H, SCH(CH$_3$)]; 1.00 (m, 3H, SCHCH$_2$CH$_3$).

Example 25 9.03 (s, 1H, COH); 7.82 (m, 5H, C$_6$H$_5$); 3.50 (m, 1H, SCH); 2.95 (d, 3H, NCH$_3$); 2.82 (d, 3H, NCH$_3$); 1.72 (m, 2H, SCHCH$_2$); 1.54 [d of d, 3H, SCH(CH$_3$)]; 1.00 (m, 3H, SCHCH$_2$CH$_3$).

Example 26 9.03 (s, 1H, COH); 3.60 (m, 1H, SCH); 3.07 (d, 3H, NCH$_3$); 3.04 (d, 3H, NCH$_3$); 1.72 (m, 2H, SCHCH$_2$); 1.50 [d, 3H, SCH(CH$_3$)]; 1.02 (t, 3H, SCHCH$_2$CH$_3$).

Example 27 9.03 (s, 1H, COH); 7.70 (m, 5H, C$_6$H$_5$); 3.50 (m, 1H, SCH); 3.08 (d, 3H, NCH$_3$); 3.06 (d, 3H, NCH$_3$); 1.78 (m, 2H, SCHCH$_2$); 1.50 [d, 3H, SCH(CH$_3$)]; 1.00 (t, 3H, SCHCH$_2$CH$_3$).

Example 28 9.00 (s, 1H, COH); 3.40 (m, 1H, SCH); 3.40 (br s, 1H); 3.00 (m, 9H, 2NCH$_3$, NHCH$_3$); 1.72 (m, 2H, SCHCH$_2$); 1.50 [d, 3H, SCH(CH$_3$)]; 1.00 (t, 3H, SCHCH$_2$CH$_3$).

TABLE II

| | | Elemental Analysis | | |
| | | Elemental Analysis Calcd. (Found) | | |
| Example | Emp. Formula | C | H | N |
|---|---|---|---|---|
| 1 | C$_{14}$H$_{23}$N$_2$O$_2$PS$_2$ | 48.55 (48.70) | 6.64 (6.82) | 8.09 (8.24) |
| 2 | C$_9$H$_{19}$N$_2$O$_4$PS$_2$ | 34.39 (34.43) | 6.05 (6.19) | 8.92 (8.99) |
| 3 | C$_8$H$_{16}$Cl$_3$N$_2$O$_2$PS$_2$ | 25.70 (25.29) | 4.28 (4.28) | 7.50 (6.99) |
| 4 | C$_{12}$H$_{26}$N$_3$O$_4$PS$_2$ | 38.81 (39.11) | 7.01 (7.45) | 11.32 (10.84) |
| 5 | C$_{11}$H$_{24}$N$_3$O$_4$PS$_2$ | 36.97 (37.68) | 6.72 (7.11) | 11.76 (11.92) |
| 6 | C$_{19}$H$_{40}$N$_3$O$_4$PS$_2$ | 48.61 (50.92) | 8.53 (9.58) | 8.1 —C$_{10}$ alkoxy. |
| 7 | C$_{12}$H$_{26}$N$_3$O$_4$PS$_2$ | 38.31 (39.53) | 7.01 (7.24) | 11.32 (11.38) |
| 8 | C$_{10}$H$_{22}$N$_3$O$_4$PS$_2$ | 34.98 (36.75) | 6.41 (6.58) | 12.24 (11.68) |
| 8a | C$_{19}$H$_{30}$N$_3$O$_5$PS$_2$ | 48.00 (51.75) | 6.52 (6.56) | 8.84 (7.62) |
| 8b | C$_{11}$H$_{24}$N$_3$O$_3$PS$_3$ | 48.00 (51.75) | 6.52 (6.56) | 8.84 (7.62) |
| 8c | C$_{16}$H$_{26}$N$_3$O$_4$PS$_2$ | 45.82 (47.51) | 6.21 (6.67) | 10.02 (9.87) |
| 8d | C$_{12}$H$_{26}$N$_3$O$_4$PS$_2$ | 45.82 (47.51) | 6.21 (6.67) | 10.02 (9.87) |
| 8e | C$_{15}$H$_{16}$N$_3$O$_2$PS$_2$ | 48.00 (47.71) | 6.93 (7.18) | 11.20 (10.73) |
| 9 | C$_8$H$_9$N$_2$O$_4$PS$_2$ | 31.79 (32.62) | 6.29 (6.58) | 9.27 (9.31) |
| 10 | C$_9$H$_{21}$N$_2$O$_4$PS$_2$ | 34.18 (33.46) | 6.64 (7.01) | 8.86 (9.08) |

TABLE II-continued

| | | Elemental Analysis Calcd. (Found) | | |
|---|---|---|---|---|
| Example | Emp. Formula | C | H | N |
| 11 | $C_{14}H_{23}N_2O_4PS_2$ | 44.44 (43.66) | 6.08 (6.51) | 7.41 (7.12) |
| 12 | $C_{10}H_{23}N_2O_4PS_2$ | 40.13 (39.90) | 7.69 (8.43) | 9.36 (10.39) |
| 13 | $C_8H_{16}F_3N_2O_4PS_2$ | 26.97 (31.85) | 4.48 (5.58) | 7.86 (7.52) |
| 14 | $C_{13}H_{21}N_2O_4PS_2$ | 42.86 (43.55) | 5.77 (5.80) | 7.69 (7.86) |
| 15 | $C_{10}H_{19}N_2O_5PS$ | 38.71 (39.85) | 6.13 (6.21) | 9.03 (8.23) |
| 16 | $C_{12}H_{23}N_2O_5PS$ | 42.60 (45.09) | 6.80 (7.10) | 8.28 (9.08) |
| 16a | $C_{10}H_{19}N_2O_5PS$ | 38.71 (39.85) | 6.13 (6.21) | 9.03 (8.23) |
| 16b | $C_{11}H_{21}N_2O_5PS$ | 40.74 (42.67) | 6.48 (6.88) | 8.64 (8.27) |
| 16c | $C_{12}H_{23}N_2O_4PS_2$ | 40.68 (42.41) | 6.50 (7.18) | 7.90 (7.27) |
| 16d | $C_{16}H_{23}N_1O_5PS$ | 49.74 (51.60) | 5.96 (6.16) | 7.25 (6.81) |
| 16e | $C_{11}H_{25}CLN_2O_5PS$ | 36.82 (38.00) | 5.57 (5.66) | 7.81 (6.61) |
| 16f | $C_{13}H_{25}N_2O_5PS$ | 44.32 (46.50) | 7.10 (7.36) | 7.95 (6.22) |
| 16g | $C_{12}H_{23}N_2O_6PS$ | 40.68 (41.76) | 6.50 (6.73) | 7.91 (6.99) |
| 16h | $C_{15}H_{27}N_2O_5PS$ | 47.61 (50.21) | 5.55 (7.52) | 7.41 (6.20) |
| 16i | $C_{12}H_{22}N_3O_5PS$ | 41.02 (42.56) | 6.27 (6.36) | 11.96 (12.02) |
| 16j | $C_{16}H_{23}N_2O_5PS$ | 47.76 (50.82) | 5.72 (5.83) | 6.97 (5.85) |
| 16k | $C_{15}H_{21}N_2O_5PS$ | 47.76 (50.82) | 5.72 (5.83) | 6.97 (5.85) |
| 17 | $C_{15}H_{23}N_2O_4PS$ | 50.28 (52.78) | 6.42 (6.70) | 7.82 (7.80) |
| 18 | $C_{10}H_{18}Cl_3N_2O_4PS$ | 30.00 (31.07) | 4.51 (4.82) | 7.01 (7.12) |
| 19 | $C_{10}H_{21}N_2O_4PS$ | 40.54 (40.58) | 7.10 (7.31) | 9.46 (9.63) |
| 20 | $C_{10}H_{19}N_2O_4PS$ | 40.82 (40.85) | 6.46 (6.46) | 9.53 (9.51) |
| 21 | NOT AVAILABLE | | | |
| 22 | $C_9H_{16}F_3N_2O_3PS$ | 28.28 (33.00) | 5.44 (5.01) | 9.46 (8.13) |
| 23 | $C_9H_{21}N_2O_2PS$ | 38.03 (37.11) | 7.29 (7.75) | 9.86 (9.70) |
| 24 | IN TEST | | | |
| 25 | $C_{14}H_{22}N_3O_5PS_2$ | 41.27 (41.27) | 5.41 (5.72) | 10.32 (9.47) |
| 26 | $C_{10}H_{17}Cl_3N_3O_4PS$ | 27.09 (29.58) | 4.12 (4.24) | 10.18 (9.68) |
| 27 | $C_{15}H_{22}N_3O_4PS$ | 48.52 (49.49) | 5.93 (6.13) | 11.32 (11.67) |
| 28 | $C_9H_{20}N_3O_3PS$ | 38.43 (37.12) | 7.12 (7.06) | 14.95 (13.43) |

BIOLOGICAL SECTION

Initial evaluations are made on the following mite, insect, and nametode:

| Code Symbol | Common Name | Latin Name |
|---|---|---|
| TSM | Two-spotted spider mite | *Tetranychus urticae* |
| SAW | Southern armyworm | *Spodoptera eridania* |
| nema | Southern root-knot nematode | *Meloidogyne incognita* |

A test solution containing 600 ppm of test compound can be made by dissolving the test compound in a solvent (acetone:methanol, 1:1), adding surfactant and then water to give an acetone:methanol:water system of 10:10:80. A 1:1 mixture of an alkylarylpolyetheralcohol (commercially available under the trademark Triton X-155) and a modified phthalic glycerol alkyl resin (commercially available under the trademark Triton B-1956) can be utilized at the equivalent of one ounce per 100 gallons of test solution and a surfactant.

For the mite test, infested bean (*Phaseolus limeanus*) leaf discs (1.25 inches in diameter) containing about 50 mites are placed in a Petri dish lid on a moistened piece of cotton. The leaves are then sprayed with the test solution using a rotating turntable. They are held for 24 hours and then the percent kill is determined.

For the armyworm test, detached bean leaves on pieces of moistened filter paper are sprayed as above for the mite test in similar dishes and allowed to dry. The dishes are infested with 10 third instar southern armyworm larvae. The dishes are covered. After holding for 48 hours, the percent kill is obtained.

For the nematode test, soil is homogeneously inoculated with a macerated blend of tomato roots heavily knotted with the root knot nematode. Ten milliliters of the test solution are added to 200 milliliters of the inoculated soil in a 16 oz. jar to give a concentration by volume of about 30 ppm. The jar is then shaken to insure thorough mixing, immediately uncapped, and allowed to air for 24 hours. The soil is then placed into a 3 inch plastic pot after which time 3 cucumber (*Cucumis sativus*) seeds are planted. About 23 days thereafter, the cucumber plants are removed from the soil and the root system examined for the presence of knots. A total of 15 knots or less is considered as a measure of control.

Table III gives the results of the foregoing biological evaluations.

TABLE III

| | Biological Evaluation Results | | |
|---|---|---|---|
| Example | TSM | SAW | NEMA |
| 1 | 100 | 100 | + |
| 2 | 100 | 100 | + |
| 3 | 100 | 100 | + |
| 4 | 100 | 100 | + |
| 5 | 100 | 100 | + |
| 6 | 100 | 100 | + |
| 7 | 100 | 100 | + |
| 8 | 100 | 100 | + |
| 9 | 100 | 100 | + |
| 10 | 79 | 100 | + |
| 11 | 100 | 20 | + |
| 12 | 100 | 100 | + |
| 13 | 100 | 100 | + |
| 14 | 100 | 80 | + |
| 15 | 100 | 100 | + |
| 16 | 100 | 100 | + |
| 17 | 100 | 0 | + |
| 18 | 100 | 90 | + |
| 19 | 100 | 100 | + |
| 20 | 100 | 100 | + |
| 21 | 100 | 100 | + |
| 22 | 100 | 100 | + |
| 23 | 100 | 60 | + |
| 24 | 100 | 100 | + |
| 25 | 100 | 100 | + |
| 26 | 100 | 20 | + |
| 27 | 100 | 100 | + |
| 28 | 100 | 100 | + |

What is claimed is:
1. A compound having the formula

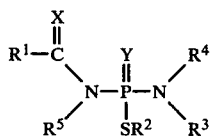

wherein
R¹ is hydrogen;
  unsubstituted or substituted $C_1$–$C_6$ alkyl wherein the substituent can be one cyano, nitro, alkoxy, alkylthio, alkylsulfinyl, alkysulfonyl, alkylcarbonyl, alkoxycarbonyl, alkylcarbonyloxy, phenoxy or phenylthio group or from one to three of the same or different bromo, chloro or fluoro groups;
  unsubstituted or substituted phenyl or naphthyl wherein the substituent can be from one to three of the same or different alkyl, haloalkyl, halo, alkoxy, alkylthio, cyano, nitro, or mono- or di-alkylamino, phenoxy, alkylsulfinyl, alkylsulfonyl, trifluoromethyl, alkoxycarbonyl, alkylcarbonyl, alkylcarbonyloxy, phenythio, phenysulfinyl, phenylsulfonyl, benzyl, phenylcarbonyl, phenylcarbonyloxy, phenylaminocarbonyl, alkenyloxycarbonyl, and alkenylcarbonyloxy wherein the alkyl moiety is straight or branched chain and contains from one to six carbon atoms
  $C_3$–$C_6$ alkenyl; and
  $C_3$–$C_8$ cycloalkyl;
R² is $C_2$–$C_6$ alkyl;
R³ and R⁵ are, independently, hydrogen, methyl or ethyl;
X and Y are, independently, O or S; and
R⁴ is
  (a) SR⁶ wherein R⁶ is unsubstituted or substituted $C_1$–$C_6$ alkyl wherein the substituent can be from one to three of the same or different chloro, bromo or fluoro groups; alkoxycarbonyl; unsubstituted or substituted phenyl or naphthyl wherein the substituent can be from one to three of the same or different alkyl, alkoxy, halo, cyano, nitro, alkylthio, alkylsulfinyl, alkylsulfonyl, phenoxy, haloalkyl, trifluoromethyl, mono- or di-alkylamino, alkylcarbonylamino, alkoxycarbonyl, alkylcarbonyl, alkylcarbonyloxy, phenylthio, phenylsulfinyl, phenylsulfonyl, benzyl, phenylcarbonyl, phenylcarbonyloxy, phenoxycarbonyl, phenylaminocarbonyl, alkenyloxycarbonyl, or alkenylcarbonyloxy, wherein the alkyl moiety is straight or branched chain and contains from one to six carbon atoms, unsubstituted or substituted amino wherein the substituent can be one or two of the same or different $C_1$–$C_6$ alkyl, unsubstituted or substituted phenyl ($C_1$–$C_5$) alkyl wherein the substituent is on the phenyl ring and wherein the substituent can be from one to three of the same or different alkyl, haloalkyl, halo, alkoxy, alkylthio, cyano, nitro, or mono- and di-alkylamino groups, wherein the alkyl moiety is straight or branched chain and contains from one to six carbon atoms;
  (b) SO₂R⁶ wherein R⁶ is as defined above;
  (c) SN(R⁷)C(=A)Z wherein R⁷ is unsubstituted or substitued $C_1$–$C_6$ alkyl wherein the substituent can be from one to three of the same or different chloro, bromo or fluoro groups or one cyano, nitro, alkoxy, alkylthio, alkylsulfinyl, alkylsulfonyl, alkylcarbonyl, alkoxycarbonyl, alkylcarbonyloxy, mono- or di-alkylaminocarbonyl, alkylcarbonylamino, phenylthio, phenylsulfinyl, phenylsulfonyl, phenoxy, phenylcarbonyl, phenylcarbonyloxy, phenoxycarbonyl, phenylaminocarbonyl, alkenyloxycarbonyl, or alkenylcarbonyloxy groups, wherein the alkyl moiety is straight or branched chain and contains from one to six carbon atoms; unsubstituted or substituted phenyl or naphthyl, or unsubstituted or substituted phenyl($C_1$–$C_5$)alkyl, wherein the substituent on the phenyl or naphthyl ring can be from one to three of the same or different cyano, nitro, halo, alkyl, alkoxy, alkylthio, alkylsulfinyl, alkylsulfonyl, phenoxy, haloalkyl, trifluoromethyl, mono- or di-alkylaminocarbonyl, alkoxycarbonyl, alkylcarbonyl, alkylcarbonyloxy, phenylthio, phenylsulfinyl, phenylsulfonyl, benzyl, phenylcarbonyl, phenyloxycarbonyl, phenylcarbonyloxy, phenylaminocarbonyl, alkenylcarbonyloxy, alkenylcarbonyloxy, aminocarbonyl, or alkylaminocarbonyl groups, wherein the alkyl moiety is straight or branched chain and contains from one to six carbon atoms; Z is unsubstituted $C_1$–$C_{10}$ alkoxy or $C_1$–$C_6$ alkoxy substituted with one alkylthio, alkoxy, or dialkylamino group, phenoxy, $C_1$–$C_6$ alkylthio, phenylthio, phenyl($C_1$–$C_5$)alkylthio, di-$C_1$–$C_6$ alkylamino, or $C_1$–$C_6$ alkyl or benzofuranyl; and A is O or S;
  (d) CO₂R⁸ wherein R⁸ is unsubstituted or substituted $C_1$–$C_6$ alkyl wherein the substituent can be from one to three bromo, chloro or fluoro groups, unsubstituted or substituted phenyl or naphthyl, or unsubstituted or substituted phenyl($C_1$–$C_3$) alkyl, wherein the substituent on the phenyl or naphthyl ring can be from one to three of the same or different cyano, nitro, halo, alkyl, alkoxy, alkylthio, alkylsulfinyl, alkylsulfonyl, phenoxy, haloalkyl, trifluoromethyl, mono- or di-alkylaminocarbonyl, alkoxycarbonyl, alkylcarbonyl, alkylcarbonyloxy, phenylthio, phenylsulfinyl, phenylsulfonyl, benzyl, phenylcarbonyl, phenoxycarbonyl, phenylcarbonyloxy, phenylaminocarbonyl, alkenylcarbonyloxy, alkenylcarbonyloxy, aminocarbonyl, or alkylaminocarbonyl groups, wherein the alkyl moiety is straight or branched chain and contains from one to six carbon atoms; or $C_2$–$C_3$ alkenyl;
  (e) C(O)-C(O)-OR⁹ wherein R⁹ is unsubstituted or substituted $C_1$–$C_{10}$ alkyl wherein the substituent can be from one to three of the same or different chloro, bromo or fluoro groups or one cyano, nitro, alkoxy, alkylthio, alkylsulfinyl, alkylsulfonyl, alkylcarbonyl, alkoxycarbonyl, alkylcarbonyloxy, mono- or di-alkylaminocarbonyl, alkylcarbonylamino, phenylthio, phenylsulfinyl, phenylsulfonyl, phenoxy, phenylcarbonyl, phenylcarbonyloxy, phenoxycarbonyl, phenylaminocarbonyl, alkenyloxycarbonyl, or alkenylcarbonyloxy groups, wherein the alkyl moiety is straight or branched chain and contains from one to six carbon atoms; unsubstituted or substituted phenyl or naphthyl or unsubstituted or substituted phenyl($C_1$–$C_3$)alkyl, wherein the substituents on the phenyl or naphthyl ring can be from one to three of the same or different cyano, nitro, halo, alkyl, alkoxy, alkylthio, alkylsulfinyl, alkylsulfonyl, phenoxy, haloalkyl, trifluoromethyl, mono- or di-alkylaminocarbonyl, alkoxycarbonyl, alkylcarbonyl, alkylcarbonyloxy, phenylthio, phenylsulfinyl, phenylsulfonyl, benzyl, phenylcarbonyl, phenoxycarbonyl, phenylcarbonyloxy, phenylaminocarbonyl, alkenylcarbonyloxy, alkenylcarbonyloxy, aminocarbonyl, or alkylaminocarbonyl groups, wherein the alkyl moiety is straight or branched chain and contains from one to six carbon atoms;

(f) C(O)-NH(B)$R^{10}$ wherein B is CO or $SO_2$; and $R^{10}$ is unsubstituted or substituted $C_1$-$C_6$ alkyl wherein the substituent can be from one to three bromo, chloro or fluoro groups; unsubstituted or substituted phenyl wherein the substituent can be from one to three of the same or different cyano, nitro, halo, alkyl, alkoxy, alkylthio, alkylsulfinyl, alkylsulfonyl, phenoxy, haloalkyl, trifluoromethyl, mono- or di-alkylaminocarbonyl, alkoxycarbonyl, alkylcarbonyl, alkylcarbonyloxy, phenylthio, phenylsulfinyl, phenylsulfonyl, benzyl, phenylcarbonyl, phenoxycarbonyl, phenylcarbonyloxy, phenylaminocarbonyl, alkenylcarbonyloxy, alkenylcarbonyloxy, aminocarbonyl, or alkylaminocarbonyl groups, wherein the alkyl moiety is straight or branched chain and contains from one to six carbon atoms;

(g) C(O)N$R^{11}R^{12}$ wherein $R^{11}$ and $R^{12}$ are, independently, hydrogen or unsubstituted or substituted $C_1$-$C_6$ alkyl wherein the substituent can be from one to three of the same or different chloro, bromo or fluoro groups or one cyano, nitro, alkoxy, alkylthio, alkylsulfinyl, alkylsulfonyl, alkylcarbonyl, alkoxycarbonyl, alkylcarbonyloxy, mono- or di-alkylaminocarbonyl, alkylcarbonylamino, phenylthio, phenylsulfinyl, phenylsulfonyl, phenoxy, phenylcarbonyl, phenylcarbonyloxy, phenoxycarbonyl, phenylaminocarbonyl, alkenyloxycarbonyl, or alkenylcarbonyloxy groups, wherein the alkyl moiety is straight or branched chain and contains from one to six carbon atoms;

(h) $(CHR^{14})_mS(O)_nR^{13}$ or $(CHR^{14})_mOR^{13}$ wherein m is 1, 2 or 3; n is 0, 1, or 2; $R^{13}$ is unsubstituted or substituted $C_1$-$C_6$ alkyl wherein the substituent can be from one to three of the same or different chloro, bromo or fluoro groups or one cyano, nitro, alkoxy, alkylthio, alkylsulfinyl, alkylsulfonyl, alkylcarbonyl, alkoxycarbonyl, alkylcarbonyloxy, mono- or di-alkylaminocarbonyl, alkylcarbonylamino, phenylthio, phenylsulfinyl, phenylsulfonyl, phenoxy, phenylcarbonyl, phenylcarbonyloxy, phenoxycarbonyl, phenylaminocarbonyl, alkenyloxycarbonyl, or alkenylcarbonyloxy groups, wherein the alkyl moiety is straight or branched chain and contains from one to six carbon atoms; unsubstituted or substituted phenyl($C_1$-$C_3$)alkyl, or unsubstituted or substituted phenyl or naphthyl, wherein the substituent on the phenyl or naphthyl ring can be from one to three of the same or different cyano, nitro, halo, alkyl, alkoxy, alkylthio, alkylsulfinyl, alkylsulfonyl, phenoxy, haloalkyl, trifluoromethyl, mono- or di-alkylaminocarbonyl, alkoxycarbonyl, alkylcarbonyl, alkylcarbonyloxy, phenylthio, phenysulfinyl, phenylsulfonyl, benzyl, phenylcarbonyl, phenoxycarbonyl, phenylcarbonyloxy, phenylaminocarbonyl, alkenylcarbonyloxy, alkenylcarbonyloxy, aminocarbonyl, or alkylaminocarbonyl groups, wherein the alkyl moiety is straight or branched chain and contains from one to six carbon atoms; and $R^{14}$ is hydrogen; unsubstituted or substituted alkyl; or unsubstituted or substituted phenyl; or (i) C(X)$R^1$ wherein X and $R^1$ are as defined above.

2. A compound according to claim 1 wherein X and Y are both O;

$R^1$ is hydrogen;
unsubstituted or substituted $C_1$-$C_6$ alkyl; or unsubstituted or substituted phenyl;
$R^2$ is $C_2$-$C_6$ alkyl;
$R^3$ and $R^5$, independently, are hydrogen or methyl;
$R^4$ is
(a) $SR^6$ wherein $R^6$ is unsubstituted or substituted $C_1$-$C_6$ alkyl; alkoxycarbonyl; or unsubstituted or substituted phenyl;
(b) $SO_2R^6$ wherein $R^6$ is unsubstituted or substituted $C_1$-$C_6$ alkyl; alkoxycarbonyl; or unsubstituted or substituted phenyl;
(c) $SN(R^7)C(=A)Z$ wherein $R^7$ is unsubstituted or substituted $C_1$-$C_6$ alkyl; unsubstituted or substituted phenyl; Z is unsubstituted $C_1$-$C_{10}$ or $C_1$-$C_6$ alkoxy substituted with one alkylthio, alkoxy, phenoxy, dialkylamino; $C_1C_6$ alkylthio; phenylthio; benzofuranyl; phenyl($C_1$-$C_5$)alkylthio; di-($C_1$-$C_6$)alkylamino; or $C_1$-$C_6$ alkyl or benzofuranyl; and A is O or S;
(d) $CO_2R^8$ wherein $R^8$ is unsubstituted or substituted $C_1$-$C_6$ alkyl; unsubstituted or substituted phenyl, or unsubstituted or substituted phenyl(-$C_1$-$C_3$)alkyl; or $C_2$-$C_3$ alkenyl;
(e) C(O)-C(O)-O$R^9$ wherein $R^9$ is unsubstituted or substituted ($C_1$-$C_{10}$)alkyl; unsubstituted or substituted phenyl, or unsubstituted or substituted phenyl($C_1$-$C_3$)alkyl;
(f) C(O)-NH(B)$R^{10}$ wherein B is CO or $SO_2$; and $R^{10}$ is unsubstituted or substituted $C_1$-$C_6$ alkyl wherein the substituent can be from one to three of the same or different bromo, chloro or fluoro groups; or unsubstituted or substituted phenyl wherein the substituent can be one to three of the same or different alkyl or halo groups;
(g) C(O)N$R^{11}R^{12}$ wherein $R^{11}$ and $R^{12}$, are independently, hydrogen or unsubstituted $C_1$-$C_6$ alkyl;
(h) $(CHR^{14})_mS(O)_nR^{13}$ or $(CHR^{14})_mOR^{13}$ wherein m is 1, 2 or 3; n is 0, 1 or 2; $R^{13}$ is unsubstituted or substituted $C_1$-$C_6$ alkyl; and $R^{14}$ is hydrogen or unsubstituted $C_1$-$C_6$ alkyl; or
(i) C(X)$R^1$ wherein
X is O; and
$R^1$ is hydrogen; unsubstituted or substituted $C_1$-$C_6$ alkyl; or unsubstituted or substituted phenyl.

3. A compound according to claim 2 wherein:
X and Y are both O;
$R^1$ is hydrogen; unsubstituted or substituted $C_1$-$C_6$ alkyl wherein the substituent can be from one to three of the same or different bromo, chloro or fluoro groups; or phenyl;
$R^2$ is $C_3$-$C_5$ alkyl;
$R^3$ and $R^5$ are each methyl; and
$R^4$ is (a) $SR^6$ wherein $R^6$ is unsubstituted or substituted $C_1$-$C_6$ alkyl wherein the substituent can be from one to three of the same or different chloro, bromo, or fluoro groups; unsubstituted or substituted phenyl wherein the substituent can be from one to three of the same or different alkyl groups; or alkoxycarbonyl;

(b) $SO_2R^6$ wherein $R^6$ is unsubstituted $C_1$-$C_6$ alkyl or trifluoromethyl, or unsubstituted phenyl;

(c) $SN(R^7)C(=A)Z$ wherein $R^7$ is unsubstituted or substituted $C_1$-$C_6$ alkyl; A is O; and Z is $C_1$-$C_{10}$ alkoxy; or benzofuranyl;

(d) $CO_2R^8$ wherein $R^8$ is unsubstituted or substituted $C_1$-$C_6$ alkyl wherein the substituent can be from one to three of the same or different bromo, chloro, or fluoro groups; unsubstituted phenyl; unsubstituted phenyl $(C_1$-$C_3)$ alkyl; and $C_2$-$C_3$ alkenyl;

(e) $C(O)$-$C(O)$-$OR^9$ wherein $R^9$ is unsubstituted or substituted $C_1$-$C_{10}$alkyl;

(f) $C(O)$-$NH(B)R^{10}$ wherein B is $C(O)$ or $SO_2$; and $R^{10}$ is unsubstituted or substituted $C_1$-$C_6$ alkyl wherein the substituent can be from one to three of the same or different bromo, chloro or fluoro groups; unsubstituted or substituted phenyl wherein the substituent can be from one to three alkyl groups;

(g) $C(O)NR^{11}R^{12}$ wherein $R^{11}$ and $R^{12}$ are, independently, hydrogen or $C_1$-$C_3$ alkyl;

(h) $(CH_2)_mSR^{13}$ or $(CH_2)_mOR^{13}$ wherein m is 1 or 2; and $R^{13}$ is unsubstituted $C_1$-$C_6$ alkyl; or (i) $C(X)R^1$ wherein X and $R^1$ are as defined above.

4. A compound according to claim 3 wherein:
X and Y are O;
$R^2$ is 1-methylpropyl;
$R_3$ and $R_5$ are each methyl; and
$R^4$ is
(a) $SR^6$ wherein $R^6$ is phenyl, 4-methylphenyl, methyl or trichloromethyl; or methoxycarbonyl;
(b) $SO_2R^6$ wherein $R^6$ is methyl, butyl, trifluoromethyl;
(c) $SN(R^7)(=A)$ wherein $R^7$ is methyl and $C(=A)Z$ is $C(O)OPr$, $C(O)Et$, $C(O)CH_3$ or $C(O)OC_{10}H_{21}$;
(d) $CO_2R^8$ wherein $R^8$ is phenylmethyl, 2-trichloroethyl, or $-CH=CH_2$;
(e) $C(O)$-$C(O)$-$OR^9$ wherein $R^9$ is methyl 1-methylethyl, ethyl, or 2-methoxyethyl
(f) $C(O)$-$NH(B)R^{10}$ wherein B is $SO_2$ or $C(O)$ and $R^{10}$ is 4-methylphenyl, phenyl, or trichloromethyl; and $R^{10}$ is 4-methylphenyl, phenyl, or trichloromethyl
(g) $C(O)NR^{11}R^{12}$ wherein $R^{11}$ is hydrogen and $R^{12}$ is methyl;
(h) $CH_2SCH_3$; or
(i) $C(X)R^1$ wherein X is O and $R^1$ is hydrogen or trifluoromethyl.

5. A compound according to claim 4 wherein:
$R^1$ is H;
$R^2$ is 1-methylpropyl;
$R^3$ is methyl;
$R^4$ is $SC(O)OCH_3$; and
$R^5$ is methyl.

6. A compound according to claim 4 wherein:
X and Y are both O;
$R^1$ is H;
$R^2$ is 1-methylpropyl;
$R^3$ is methyl;
$R^4$ is $S$-$C_6H_4$-$CH_3$-p; and
$R^5$ is methyl.

7. A compound according to claim 4 wherein:
X and Y are both O;
$R^1$ is H;
$R^2$ is 1-methylpropyl;
$R^3$ is methyl;
$R^4$ is $SO_2CH_3$ and
$R^5$ is methyl.

8. A compound according to claim 4 wherein:
X and Y are both O;
$R^1$ is H;
$R^2$ is 1-methylpropyl;
$R^3$ is methyl;
$R^4$ is $SO_2CF_3$ and
$R^5$ is methyl.

9. A compound according to claim 4 wherein:
X and Y are both O;
$R^1$ is H;
$R^2$ is 1-methylpropyl;
$R^3$ is methyl;
$R^4$ is $S$-$N(CH_3)$-$C(O)O$-$CH(CH_3)_2$; and
$R^5$ is methyl.

10. A compound according to claim 4 wherein:
X and Y are both O;
$R^1$ is H;
$R^2$ is 1-methypropyl;
$R^3$ is methyl;
$R^4$ is $S$-$N[CH(CH_3)_2]$-$C(O)O$-$CH_3$; and
$R^5$ is methyl.

11. A compound according to claim 4 wherein:
X and Y are both O;
$R^1$ is H;
$R^2$ is 1-methylpropyl
$R^3$ is methyl;
$R^4$ is $S$-$N(CH_3)$-$C(O)O$-$Pr$,
and
$R^5$ is methyl.

12. A compound according to claim 4 wherein:
X and Y are both O;
$R^1$ is H;
$R^2$ is 1-methylpropyl;
$R^3$ is methyl;
$R^4$ is $C(O)$-$C(O)O$-$CH(CH_3)_2$; and
$R^5$ is methyl.

13. A compound according to claim 4 wherein:
X and Y are both O;
$R^1$ is H;
$R^2$ is 1-methylpropyl;
$R^3$ is methyl;
$R^4$ is $C(O)C(O)OCH_2CH_2OCH_3$; and
$R^5$ is methyl.

14. A compound according to claim 4 wherein:
X and Y are both O;
$R^1$ is H;
$R^2$ is 1-methylpropyl;
$R^3$ is methyl;
$R^4$ is $C(O)C(O)OCH_2CH_3$; and
$R^5$ is methyl.

15. A compound according to claim 4 wherein:
X and Y are both O;
$R^1$ is H;
$R^2$ is 1-methylpropyl;
$R^3$ is methyl;
$R^4$ is $CH_2SCH_3$,
and
$R^5$ is methyl.

16. A compound according to claim 4 wherein:

X and Y are both O;
R$^1$ is H;
R$^2$ is 1-methylpropyl;
R$^3$ is methyl;
R$^4$ is CH$_2$OCH$_3$,
and
R$^5$ is methyl.

17. A compound according to claim 4 wherein:
X and Y are both O;
R$^1$ is H;
R$^2$ is 1-methylpropyl;
R$^3$ is methyl;
R$^4$ is C(O)-H,
and
R$^5$ is methyl.

18. A compound according to claim 4 wherein:
X and Y are both O;
R$^1$ is H;
R$^2$ is 1-methylpropyl;
R$^3$ is methyl;
R$^4$ is C(O)-CF$_3$,
and
R$^5$ is methyl.

19. A compound according to claim 4 wherein:
X and Y are both O;
R$^1$ is H;
R$^2$ is 1-methylpropyl;
R$^3$ is methyl;
R$^4$ is C(O)O-CH=CH$_2$,
and
R$^5$ is methyl.

20. A compound according to claim 4 wherein:
X and Y are both O;
R$^1$ is H;
R$^2$ is 1-methylpropyl;
R$^3$ is methyl;
R$^4$ is C(O)-CH$_2$CH$_3$,
and
R$^5$ is methyl.

21. A method of controlling pests comprising contacting the pests with a pesticidally effective amount of a compound according to claim 1.

22. A method of controlling pests comprising contacting the pests with a pesticidally effective amount of a compound according to claim 4.

23. A pesticidal composition comprising a pesticidally effective amount of a composition according to claim 1 and an agronomically acceptable carrier.

24. A pesticidal composition comprising a pesticidally effective amount of a composition according to claim 4 and an agronomically acceptable carrier.

* * * * *